(12) United States Patent
Njar et al.

(10) Patent No.: US 7,265,143 B2
(45) Date of Patent: Sep. 4, 2007

(54) C-4 SUBSTITUTED RETINOIDS

(75) Inventors: Vincent C. O. Njar, Columbia, MD (US); Angela M. H. Brodie, Fulton, MD (US); Ivo P. Nnane, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 447 days.

(21) Appl. No.: 10/339,332

(22) Filed: Jan. 10, 2003

(65) Prior Publication Data

US 2003/0162823 A1    Aug. 28, 2003

Related U.S. Application Data

(63) Continuation-in-part of application No. PCT/US01/16524, filed on Jul. 11, 2001.

(60) Provisional application No. 60/217,465, filed on Jul. 11, 2000.

(51) Int. Cl.
  *A61K 31/415* (2006.01)
  *A61K 31/215* (2006.01)
  *C07D 233/00* (2006.01)
  *C07D 229/00* (2006.01)
  *C07D 53/00* (2006.01)

(52) U.S. Cl. ............ 514/396; 514/529; 514/559; 548/335.1; 554/103; 554/221

(58) Field of Classification Search .......... 514/396, 514/529, 559; 548/335.1; 554/103, 221
See application file for complete search history.

(56) References Cited

U.S. PATENT DOCUMENTS 5,124,083 A    6/1992   Shealy
5,808,120 A    9/1998   DeLuca et al.

OTHER PUBLICATIONS

Barua et al. *Preparation and Properties of 4-Oxo-Retinoic Acid and its Methylester.* Tetrahedron Letters. No. 18. pp. 1823-1825. 1972.
Patel, et al., "Novel Retinoic Acid Metabolism Blocking Agents (RAMBAs) Endowed with Multiple Biological Activities Are Efficient Growth Inhibitors of Human Breast and Prostate Cancer Cells In Vitro and a Human Breast Tumor Xenograft in Nude Mice," UNPUBLISHED.

(Continued)

*Primary Examiner*—Taylor Victor Oh

(57) ABSTRACT

C-4 substituted retinoic acid analogs, synthesis methods of C-4 substituted retinoic acid analogs and methods of using C-4 substituted retinoic acid analogs to treat various cancers and dermatological diseases and conditions. The C-4 substituted retinoic acid analogs include C-4 all-trans retinoic acid (ATRA) and 13-cis retinoic acid (13-CRA) analogs. The C-4 substituted retinoic acid analogs inhibit all-trans retinoic acid (ATRA) 4-hydroxylase activity, thereby inhibiting the catabolism of ATRA. The C-4 substituted retinoic acid analogs also have ATRA-mimetic activity. The preferred substitutions at C-4 are an azole group, a sulfur, oxygen, or nitrogen containing group, a pyridyl group, an ethinyl group, a cyclopropyl-amine group, an ester group, or a cyano group, or forms, together with the C-4 carbon atom, an oxime, an oxirane or aziridine group.

37 Claims, 18 Drawing Sheets

OTHER PUBLICATIONS

Hong et al., "Retinoids and Human Cancer", 2nd Edition The Retinoids: Biology, Chemistry and Medicine, 2nd edition, Edited by M. B. Sporn, A.B. Roberts and D.S. Goodman, Raven Press, Ltd., New York, pp. 597-630, 1994.

Peck et al., "Synthetic Retinoids in Dermatology" The Retinoids: Biology, Chemistry and Medicine, 2nd edition, Edited by M. B. Sporn, A.B. Roberts and D.S. Goodman, Raven Press, Ltd., New York, 1994. (pp. 631-658).

Thacher et al. , "New Dermatological Agents for the Treatment of Psoriasis, Retinold Research" Journal of Medicinal Chemistry, vol. 44, No. 3, pp. 280-297, Feb. 1, 2001.

Altucci et al.., "The Promise of Retinoids to Fight Against Cancer", Nature Reviews, vol. 1, pp. 181-193, Dec. 2001.

Mangelsdorf et al., "The Retinoid Receptors." The Retinoids: Biology, Chemistry and Medicine, 2nd edition, Edited by M. B. Sporn, A.B. Roberts and D.S. Goodman, Raven Press, Ltd., New York, 1994, (pp. 319-349).

Castaigne et al. , "All-Trans Retinoic Acid as a Differentiation Therapy for Acute Promyelocytic Leukemia I. Clinical Results." Blood, vol. 76, No. 9, pp. 1704-1709, Nov. 1, 1990.

Miller, "The Emerging Role of Retinoids and Retinoic Acid Metabolism Blocking Agents in the Treatment of Cancer," Cancer, vol. 83, No. 8, pp. 1471-1482, Oct. 15, 1998.

Roberts et al., "In Vitro Metabolism of Retinoic Acid in Hamster Intestine and Liver," The Journal of Biological Chemistry, vol. 254, No. 14, pp. 6296-6302, Jul. 25, 1979.

Blaner et al., "Retinol and Retinoic Acid Metabolism," The Retinoids: Biology, Chemistry and Medicine, 2nd edition Edited by M. B. Sporn, A.B. Roberts and D.S. Goodman, Raven Press, Ltd., New York, 1994, pp. 229-255.

Nadin et al., "Participation of CYP2C8 in Retinoic Acid 4-Hydroxylation in Human Hepatic Microsomes," Biochemical Pharmacology, vol. 58, pp. 1201-1208, 1999.

McSorley et al., "Identification of Human Cytochrome P450 Isoforms that Contribute to All-trans-Retinoic Acid 4-Hydroxylation," Biochemical Pharmacology, vol. 60, pp. 517-526, 2000.

White et al., "Identification of the Retinoic Acid-inducible All-trans-retinoic Acid 4-Hydroxylase," The Journal of Biological Chemistry, vol. 271, No. 47, pp. 29922-29927, Nov. 22, 1996.

Kizaki et al. , "Mechanisms of Retinoid Resistance in Leukemic Cells: Possible Role of Cytochrome P450 and P-Glycoprotein," Blood, vol. 87, No. 2, pp. 725-733, Jan. 15, 1996.

White et al, "cDNA Cloning of Human Retinoic Acid-metabolizing Enzyme (hP450RA1) Identifies a Novel Family of Cytochromes P450 (CYP26)", The Journal of Biological Chemistry, vol. 272, No. 30, pp. 18538-18541, Jul. 25, 1997.

Ray, et al., "CYP26, A Novel Mammalain Cytochrome P450, Is Induced by Retinoic Acid and Defines a New Family" The Journal of Biological Chemistry, vol. 272, No. 30, pp. 18702-18708, Jul. 25, 1997.

Fujii et al., "Metabolic inactivation of retinoic acid by a novel P450 differentially expressed in developing mouse embryos," The EMBO Journal, vol. 16, No. 14, pp. 4163-4173, 1997.

Abul-Abed et al., "Mouse P450 RAI (CYP26) Expression and Retinoic Acid-inducible Retinoic Acid Metabolism in F9 Cells Are Regulated by Retinoic Acid Receptor $\gamma$ and Retinoid X Receptor $\alpha$*," The Journal of Biological Chemistry, vol. 273, No. 4, pp. 2409-2415, Jan. 23, 1998.

Sonneveld, et al., "Human Retinoic Acid (RA) 4-hydroxylase (CYP26) is highly specific for all trans-RA and can be induced through RA receptors in human breast and colon carcinoma cells," Cell Growth & Differentiation, vol. 9, Issue 8, pp. 629-637; Copyright 1998.

Marikar et al., "Retinoic Acid Receptors Regulate Expression of Retinoic Acid 4-Hydroxylase that Specifically Initiatives All-Trans Retinoic Acid in Human Keratinocyte HaCaT Cells," Journal of Investigative Dermatology, vol. 111, Issue 3, pp. 434-439, Sep. 1998, Abstract.

Nelson, "A Second CYP26 P450 in Humans and Zebrafish: CYP26B1", Archives of Biochemistry and Biophysics, vol. 371, No. 2, pp. 345-347, Nov. 15, 1999.

Makin et al., "Target cell metabolism of 1,25-dihydroxyvitamin D3 to calcitroic acid. Evidence for a pathway in kidney and bone involving 24-oxidation ," Biochemical Journal, 262 (173-180), 1989.

Pijnappel et al. "The retinoid ligand 4-oxo-retinoic acid is a highly active modulator of positional specification," Nature,366, 340-344, 1993.

Roos et al., "Expression of Retinoic acid 4-hydroxylase (CYP26) during mouse and *Xenopus laevis* embroyogenesis," Mechanisms of Development, 82, (1999) 203-211.

Moon et al., Retinoids and Cancer in Experimental Animals, The Retinoids: Biology, Chemistry and Medicine, 2nd edition, pp. 573-595, 1994.

Warrell, "Retinoid Resistance in Acute Promyclocytic Leukemia: New Mechanisms, Strategies, and Implications," Blood, vol. 82, No. 7, pp. 1949-1953, Oct. 1, 1993.

Reichman, et al. "Serum vitamin A and subsequent development of prostate cancer in the first National Health and Nutrition Examination Survey Epidemiologic Follow-up Study," Cancer Research, vol. 50, Issue 8, 2311-2315, 1990.

Pasquali et al., "Changes in Tissue Transglutaminase Activity and Expression during Retinoic Acid-Induced Growth Arrest and Apoptosis in Primary Cultures of Human Epithelial Prostate Cells," The Journal of Clinical Endocrinology & Metabolism, vol. 84, No. 4, pp. 1463-1469, 1999.

White, et al. P450RA1 (CYP26A1) Maps to Human Chromosome 10q23-q24 and Mouse Chromosone 19C2-3, Genomics 48, 270-272 Article No. GE975157, 1998.

Gray et al., "Loss of the Chromosomal region 10q23-25 in prostate cancer," Cancer Research vol. 55, Issue 21, 4800-4803, 1995.

Wauwe et al.. "Liarozole, an inhibitor of retinoic acid metabolism, exerts retinoid-mimetic effects in vivo," Pharmacology and Experimental Therapeutics, vol. 261, Issue 2, pp. 773-779, May 1, 1992.

Stearns et al. "Liarozole and 13-cis-retinoic acid anti-prostatic tumor activity," Cancer Research, vol. 53, Issue 13, 3073-3077, 1993.

Acevedo et al. "Liarozole potentiates the cancer chemopreventive activity of and the up-regulation of gap junctional communication and connexin43 expression by retinoic acid and beta-carotene in 10T½ cells" Carcinogenesis, vol. 16m 2215-2222, 1995.

Kelloff et al. "Aromatase Inhibitors as potential cancer chemopreventives," Cancer Epidemiology Biomakers & Prevention, vol. 7, Issue 1, 65-78, 1998.

Debruyne et al. "Liarozole—A Novel Treatment Approach For Advanced Prostate Cancer: Results of a Large Randomized Trial Versus Cyproterone Acetate," Urology 52 (1), pp. 72-81, 1998, Abstract.

Njar, "Cytochrome P450 Retinoic Acid 4-Hydroxylase Inhibitors: Potential Agents for Cancer Therapy," Mini: Reviews in Medicinal Chemistry , 2, 261-269, 2002.

Wouters et al., "Effects of liarozole, a new antitumoral compound, on retinoic acid-induced inhibition of cell growth and on retinoic acid metabolism in MCF-7 human breast cancer cells" Cancer Research, vol. 52, Issue 10, 2841-2846, 1992.

Van Wauwe et al., "Is There a Case for P-450 Inhibitors in Cancer Treatment?" Journal of Medicinal Chemistry, vol. 32, No. 10, pp. 2231-2239, 1989.

De Coster et al. "P-450 Dependent Enzymes as Targets for Prostate Cancer Therapy", J. Steroid Biochem, Molec. Biol., vol. 56, Nos. 1-6, pp. 133-143, 1996.

Njar et al., "Inhibitors of 17 $\alpha$-Hydroxylase/17,20-Lyase (CYP17): Potential Agents for the Treatment of Prostate Cancer," Current Pharmaceutical Design, 5, pp. 163-180, 1999.

Njar et al., "Inhibitors of cytochrome P450 enzymes: Their role in prostate cancer therapy" Oncologic, Endocrine & Metabolic Investigational Drugs, 1(5):495-506, 1999.

Njar et al. "Novel 4-AZOLYL Retinoic Acid Analogs: Potent Inhibitors of Retinoic Acid Metabolism Enzyme(s)" Department of Pharmacology & Experimental Therapeutics, University of Maryland, Baltimore—1999.

Njar et al. "Potent Inhibition of Retinoic Acid Metabolism Enzyme(s) by Novel Azolyl Retinoids," Bioorganic & Medicinal Chemistry Letters, 10 pp. 1905-1908, 2000.

Njar, "High-Yield Synthesis of Novel Imidazoles and Triazoles from Alcohols and Phenols," Synthesis, No. 14, 2019-2028, ISSN 0039-7881, 2000.

Stoppie et al. "R115866 Inhibits All-trans Retinoic Acid Metabolism and Exerts Retinoidal Effects in Rodents," The Journal of Pharmacology and Experimental Therapeutics, (JPET) vol. 293, No. 1, pp. 304-312, 2000.

Muindi et al. "Continuous Treatment with All-Trans Retinoic Acid Causes a Progressive Reduction in Plasma Drug Concentrations: Implications for Relapse and Retinoid "Resistance" in Patients with Acute Promyelocytic Leukemia" Blood, vol. 79, No. 2, pp. 299-303, Jan. 15, 1992.

C-4 SUBSTITUTED RETINOIDS

This is a continuation in part of International Application Number PCT/US01/16524, with an international filing date of Jul. 11, 2001, which claims priority from Provisional U.S. Application No. 60/217,465, filed Jul. 11, 2000.

The invention was made with support of grants from US Army DOD Breast Cancer Concept Award—DAMD 17-01-1-0549; the Peer Reviewed Medical Research Program, PRMRP, DOD (W81XWH-04-1-0101): and the National Institutes of Health (R21 grant—1R21CA117991). The U.S. government has certain rights in this invention.

BACKGROUND OF INVENTION

1. Field of Invention

This invention relates to novel retinoic acid analogs that have substitutions at C-4 (hereafter referred to as C-4 substituted retinoic acid analogs except otherwise stated). This invention also relates to methods of synthesis of these novel C-4 substituted retinoic acid analogs and methods of using these novel C-4 substituted retinoic acid analogs as therapeutic agents for cancers and dermatological diseases and conditions. This invention also relates to pharmaceutical compositions containing these novel C-4 substituted retinoic acid analogs.

Preferably, the novel C-4 retinoic acid analogs are all-trans retinoic acid (ATRA) and 13-cis retinoic acid (13-CRA) analogs.

2. Description of the Related Art

All-trans retinoic acid (ATRA), the biologically most active metabolite of vitamin A, plays a major role in cellular differentiation and proliferation of epithelial tissues. Differentiating agents, such as ATRA, redirect cells towards their normal phenotype and therefore may reverse or suppress evolving malignant lesions or prevent cancer invasion (Hill D L and Grubbs C J, *Retinoids and cancer prevention*, Annu Rev Nutr 12: 161-181, 1992; Hong W K and Itri L, *Retinoids and human cancer*, In *The Retinoids: Biology, Chemistry and Medicine*, Sporn M B, Roberts A B and Goodman D S (eds), pp 597-630, Raven Press: New York, 1994). However, the therapeutic effects of ATRA are undermined by its rapid in vivo catabolism by cytochrome P450-dependent enzymes (Muindi J, Frankel S R, Miller W H Jr, Jakubowski A, Scheinberg D A, Young C W, Dmitrovsky E and Warrell R P Jr, *Continuous treatment with all-trans retinoic acid causes a progressive reduction in plasma drug concentrations: implications for relapse and retenoid "resistance" in patients with acute promylocytic leukemia*, Blood 79: 299-303, 1992; Smith M A, Parkinson D R, Cheson B D and Friedman M A, *Retinoids in cancer chemotherapy*, J Clin Oncol 10: 839-864, 1992; Warrell R P Jr., *Differentiating agents*, In *Cancer, principles and practice of oncology*; DeVita Jr, Hellman S and Rosenberg S A (eds), Vol. I, pp 483-490, Lippincott: Philadelphia, 1997; Kizaki et al., 1996).

In addition, ATRA is known to have therapeutic effects for many dermatological diseases. Again, the fast catabolism of ATRA has limited the usefulness of the compound for treatment. (Cunliffe, 1986; Griffiths CEM, Fischer G J, Finkel L J, Voorhees J J, *Mechanism of action of retinoic acid in skin repair*, BR Journal of Dermatology, 127 (Suppll):21-24, 1992).

ATRA can be metabolized through several routes. The physiologically most prominent pathway starts with hydroxylation at the 4-position of the cyclohexenyl ring, leading to the formation of 4-hydroxy-ATRA that is converted to more polar metabolites via 4-oxo-ATRA (Frolik C A, Roberts A B, Tavela T E, Roller P P, Newton D L and Sporn M B, *Isolation and identification of 4-hydroxy-and 4-oxo-retinoic acid, In vitro metabolites of all-trans-retinoic acid in hamster trachea and liver*, Biochemistry 18: 2092-2097, 1979; Frolik C A, Roller P P, Roberts A B and Sporn M B, *In vitro and in vivo metabolism of all-trans-and 13-cis-retinoic acid in hamsters*, J Biol chem 255: 8057-8062, 1980; Roberts A B, Nichols M D, Newton D L and Sporn M B, *In vitro metabolism of retinoic acid in hamster intestine and liver*, J Biol Chem 254: 6296-6302, 1979; Roberts A B, Lamb L C and Sporn M B, *Metabolism of all-trans-retinoic acid in Hamster liver microsomes: oxidation of 4-hydroxy-to 4-keto-retinoic acid*, Arch Biochem Biophys 199: 374-383, 1980; Van Wauwe J, Coene M-C, Cools W, Goosens J, Lauwers W, Le Jeune L, van Hove C and van Nyen G, *Liarozole-fumarate inhibits the metabolism of 4-keto-all-trans-retinoic acid*, Biochem Pharmacol 47: 737-741j, 1994; Napoli J L, *Retinoic acid biosynthesis and metabolism*, FASEB J 10: 993-1001, 1996). The first and third catabolic steps are catalyzed by a cytochrome P450-dependent enzyme complex (Frolik C A, Roller P P, Roberts A B and Sporn M B, *In vitro and in vivo metabolism of all-trans-and 13-cis-retinoic acid in hamsters*, J Biol chem 255: 8057-8062, 1980; Leo M A, Lida S and Lieber C S, *Retinoic acid metabolism by a system reconstituted with cytochrome P450*, Arch Biochem Biophys 243: 305-312, 1984; Van Heusden J, Wouters W, Ramackers F C S, Krekels M D W G, Dillen L, Borgers M and Smets G, *All-trans-retinoic acid metabolites significantly inhibit the proliferation of MCF-7 human breast cancer cells in vitro*, Br J Cancer 77: 26-32, 1998a; Van Heusden J, Wouters W, Ramackers F C S, Krekels M D W G, Dillen L, Borgers M and Smets G, *All-trans-retinoic acid metabolites significantly inhibit the proliferation of MCF-7 human breast cancer cells in vitro*, Br J Cancer 77: 1229-1235, 1998b). Although the exact nature of this enzyme remains to be elucidated, a cytochrome P450 enzyme (designated CYP26) with specific ATRA 4-hydroxylase activity, which is also rapidly induced by ATRA has recently been cloned from zebra fish, mouse and man (for reviews, see Haque M, Andreola F, DeLuca L M, *The cloning and characterization of a novel cytochrome P450 family, CYP26, with specificity towards retinoic acid*, Nutri Rev 56:84-85, 1999; Sonneveld E and Vander Sagg P T, *Metabolism of retinoic acid: implications for development and cancer*, Inter. J Vit Nutr Res 68: 404-410, 1998).

Initially, the 4-hydroxylase activity was thought to mainly reside in the liver (Roberts A B, Lamb L C and Sporn M B, *Metabolism of all-trans-retinoic acid in Hamster liver microsomes: oxidation of 4-hydroxy-to 4-keto-retinoic acid*, Arch Biochem Biophys 199: 374-383, 1980), but its presence has now been demonstrated in skin and tumor cells and tissues (Vanden Bossche H, Willemsens G, *Retinoic acid and cytochrome P450*, In *Retinoids: 10 Years On*. Saurat J H (ed). pp 79-88, Karger: Basel, 1990; Varani J, Gendimenico G A, Hhah B, Gibbs D, Capetola R J, Mezick J A and Voorhess J J, *A direct comparison of pharmacologic effects of retinoids on skin cells in vitro and in vivo*, Skin Pharmacol 4: 254-261, 1991; Wouters W, Van Dun J, Dillen A, Coene M. C, Cools W and De Coster R, *Effects of liarozole, a new antitumoral compound an retinoic acid-induced inhibition of cell growth and on retinoic acid metabolism in MCF-7 breast cancer cells*, Cancer Res 52: 2841-2846, 1992; Krekels M D W G, Zimmerman J, Janssen B, Van Ginckel R, Van Hove C, Coene M.-C and Wouter W, *Analysis of the* oxidative catabolism of retinoic acid in rat Dunning R 3327G prostate tumors, Prostate 29: 36-41, 1996).

In principle, inhibitors of 4-hydroxylase should increase endogenous levels of ATRA (acting as 'ATRA-mimetics') and overcome some ATRA-resistance. A number of azole compounds which inhibit several cytochrome P450 enzymes have also been shown to be inhibitors of ATRA 4-hydroxylase (Williams J B and Napoli J L, *Metabolism of retinoic acid and retinol during differentiation of F9 embryonal cells, Proc Natl Acad Sci USA* 82: 4658-4662, 1985; Williams J B and Napoli J L, *Inhibition of retinoic acid metabolism by imidazole antimycotics in F9 embroynal carcinoma cells, Biochem Pharmacol* 36: 1386-1388, 1987; Napoli J L, *Retinoic acid biosynthesis and metabolism, FASEB J* 10: 993-1001, 1996; Roberts A B, Nichols M D, Newton D L and Spom M B, *In vitro metabolism of retinoic acid in hamster intestine and liver, J Biol Chem* 254: 6296-6302, 1979; Vanden Bossche H, Willemsens G and Janssen P A J, *Cytochrome-P-450-dependent metabolism of retinoic acid in rat skin microsomes: Inhibition by ketoconazole, Skin Pharmacology* 1: 176-185, 1988; Van Wauwe J P, Coene M C, Goossens J, Van Nijen G, Cools W, Lauwers W, *Ketoconazole inhibits the in vitro and in vivo metabolism of all-trans-retinoic acid, J Pharmacol Exp Ther,* 245:718-722, 1988; Freyne E, Raeymaekers A, Venet M, Sanz G, Wouters W, De Coster R and Van Wauwe J, *Synthesis of Liazal™, a retinoic acid metabolism blocking agent (RAMBA) with potential clinical applications in oncology and dermatology, Bioorg Med Chem Lett* 8: 267-272, 1998). The discovery of retinoic acid metabolism blocking agents (RAMBAs) have led to interest of using RAMBAs in the treatments of cancers. (Miller, Jr., W. H., *The Emerging Role of Retinoids and Retinoic Acid Metabolism Blocking Agents in the Treatment of Cancer, Cancer,* 83, 1471-1482, 1998). Inhibitors of retinoic acid metabolism are known as retinoic acid metabolism blocking agents or "RAMBAs".

Liarozole fumarate (LIAZAL™), a (1H-imidaz-1-ylmethyl)-1H-benzimidazole derivative, is one of the first new generation RAMBAs in clinical practice. Liarozole fumarate may soon be approved for the treatment of prostate cancer. (see, Waxman J. Roylance R., *Editorial: New Drugs for Prostate Cancer? Eur. J. Cancer,* 34, 437, 1998; and Debruyne, F. J. M. et al., *Liarozole-A Novel Treatment Approach for Advanced Prostate Cancer: Results of a Large Randomized Trial versus Cyproterone, Urology,* 52, 72-81, 1998)

Studies of liarozole's pharmacodynamics revealed that it inhibits ATRA 4-hydroxylase. (De Coster R, Wouters W, Van Ginckel R, End D, Krekels M, Coene M. -C and Bowden C, *Experimental studies with liarozole (R75251): an antitumoral agent which inhibits retinoic acid breakdown, J Steroid Biochem Molec Biol* 43: 197-201, 1992) However, the FDA's review of phase III trial data for liarozole in prostate cancer was negative. Although clinical efficacy was seen, the activity/toxicity ratio was considered insufficient. Hence Janssen Pharmaceutica NV, liarozole's manufacturer, has discontinued clinical development of liarozole (Wouters W (2000) *Personal communication*; Njar V C O and Brodie A M H, *Inhibitors of cytochrome P450 enzymes: Their role in prostae cancer therapy, I Drugs* 1: 495-506, 1999c). It appears that the reason for the high toxicity was that liarozole inhibits ATRA 4-hydroxylase only at micromolar concentrations, and at those levels it also exhibits harmful inhibitory activity with other cytochrome P450 enzymes (Bruynseels et al., 1990). The adverse side-effects of liarozole in the treatment of prostate cancer may be caused by a lack of selectivity for and/or potent inhibition of ATRA 4-hydroxylase enzyme.

Because of therapeutic benefits of liarozole for prostate cancer are limited by its side-effects, it would be useful to have compounds that inhibit ATRA 4-hydroxylase in nanomolar concentrations and have greater specificity for ATRA 4-hydroxylase than liarozole. Such compounds may avoid the harmful side-effects of liarozole and be tolerated better. Such compounds may also be useful in the treatment of other types of cancers and various dermatological conditions.

Thus, this invention helps overcome the problems of treating cancers and dermatological diseases and dermatological conditions with novel compounds that block catabolism of all-trans retinoic acid. These novel compounds have higher specificity to enzymes involved in retinoic acid catabolism and lower toxicity for the patient. Selective and potent inhibitory compounds of ATRA catabolism, using nanomolar concentration of the compounds, result in effective modulation to desirable levels of ATRA, either endogenous ATRA or of ATRA mimetic compounds. With higher levels of ATRA, the patient will have improved prognosis and outcomes.

The novel compounds in this invention are ATRA and 13-CRA analogs that have substitutions at the C-4.

BRIEF SUMMARY OF THE INVENTION

This invention is a novel chemical compound having the formula (I)

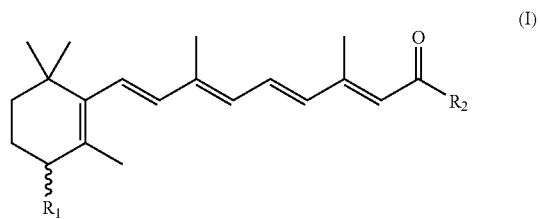

In formula (I), $R_1$ is an azole group, a sulfur, oxygen, or nitrogen containing group, a pyridyl group, an ethinyl group, a cyclopropyl-amine group, an ester group, or a cyano group, or $R_1$ forms, together with the C-4 carbon atom, an oxime, an oxirane or aziridine group; and $R_2$ is a hydroxyl group, an aminophenol group, an ester group, or an azole group.

$R_1$ may be a sulfur containing group. Examples of such sulfur containing groups include thiirane, thiol and alkylthiol derivatives. Examples of such alkylthiol derivatives include $C_1$ to $C_{10}$ alkyl thiols.

$R_1$ may be an oxygen containing group. Examples of oxygen containing groups include —$OR_4$, where $R_4$ is hydrogen or an alkyl group (preferably a 1-10 carbon alkyl, more preferably methyl or ethyl), cyclopropylether or an oxygen containing group that forms, together with the 4-position carbon, an oxirane group.

$R_1$ may be a nitrogen containing group. Examples of such nitrogen containing groups include the formula —$NR_5R_6$, where $R_5$ and $R_6$ are independently selected from the group consisting of hydrogen and alkyl groups (preferably a 1-10 carbon alkyl, more preferably methyl or ethyl), or $R_5$ and $R_6$ may together form a ring. Preferably the ring formed by $R_5$ and $R_6$ is a imidazolyl ring or a triazole ring.

Preferable azole substituent groups include imidazoles and triazoles, including attached through a nitrogen ring atom. More preferably, the azole substituent groups include 1H-imidazole-1-yl, 1H-1,2,4-triazol-1-yl and 4H-1,2,4-triazol-1-yl.

$R_1$ may be a cyano, amino, azido, cyclopropylamino, or $R_1$ is a nitrogen containing group that forms, together with the 4-position carbon, an aziridine group or an oxime group.

$R_1$ may also be a pyridyl group or an allylic azole group, preferably methyleneazolyl.

The definitions for $R_1$ of an ester includes substituent groups that contain an ester moiety, including substituent groups attached via an ester moiety.

$R_2$ may be preferably selected from the group consisting of hydroxyl, aminophenol, —$OR_3$ and azole groups, wherein $R_3$ is selected from the group consisting of alkyl, aryl and heterocyclic groups, more preferably, hydroxyl or —$OCH_3$ (methoxy).

Said alkyl substituents for the above identified substituent groups include substituted and unsubstituted alkyl groups, branched and straight chain and cyclo alkyl groups, such as cyclopropyl.

The term "aryl" includes a phenyl or naphthyl ring.

The term "heterocyclic group" includes an unsubstituted or substituted stable 3- to 7-membered monocyclic or 7- to 10-membered bicyclic heterocyclic ring and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quaternized and including a bicyclic group in which any of the above-defined heterocyclic rings is fused to a benzene ring. The heterocyclic ring may be attached at any heteroatom or carbon atom which affords a stable structure. The hetercyclic group may be saturated or unsaturated.

Examples of heterocyclic groups include piperidinyl, piperazinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoazolyl, furyl, tetrahydrofuryl, tetrahydropyranyl, thienyl, benzothienyl, thiamorpholinyl, thiamorpholinylsulfoxide, thiamorpholinylsulfone, oxadiazolyl, triazolyl, tetrahydroquinolinyl, and tetrahydroisoquinolinyl.

Table 1 shows the chemical structure of some of the compounds according to the present invention.

TABLE 1

| Compound | $R_1$ | $R_2$ |
|---|---|---|
| VN/12-1[t] | 1 H-imidazole | —$OCH_3$ |
| VN/13-1[t] | 1 H-1,2,4-triazole | —$OCH_3$ |
| VN/13-2[t] | 2 H-1,2,4-triazole | —$OCH_3$ |
| VN/14-1[t] | 1 H-imidazole | —OH |
| VN/16-1[t] | 1 H-1,2,4-triazole | —OH |
| VN/17-1[t] | 2 H-1,2,4-triazole | —OH |
| VN/50A-1[t] | 1 H-imidazole | 1 H-imidazole |
| VN/51A-1[t] | Keto oxime | —$OCH_3$ |
| VN/66-1[t] | 1 H-imidazole | —$NHC_6H_4OH$ |
| VN/65-4* | 1 H-imidazole | —$OCH_3$ |
| VN/67-1* | 1 H-imidazole | —OH |
| VN/68-1* | 1 H-imidazole | 1 H-imidazole |
| VN/69-1* | 1 H-imidazole | —$NHC_6H_4OH$ |

[t] = All-trans compounds.
*VN/65-4, VN/67-1, VN/68-1 and VN/69-1 are C-4 substituted 13-cis retinoic acid analogs.

Preferred compounds include (±)-4-(1H-imidazol-1-yl)-13-cis-methylreti noate (VN/65-4), (±)-4-(1H-imidazol-1-yl), N-(4'-hydroxyphenyl)retinamide (VN/66-1) and VN/50A-1.

The precursors for VN/65-4 and VN/66-1 are those of 13-cis-retinoic acid (13-CRA) and fenretinide, respectively (see FIGS. 1 and 14). These compounds have long elimination half-lives in most animal species, and thus are believed to have improved pharmacokinetic (PK) parameters. PK data for VN/65-4 and VN/66-1 are shown in Table 3 herein. VN/65-4 and VN/66-1 have excellent ATRA 4-hydrozylase inhibitory activity and favorable pharmacokinetic properties.

It is an object of this invention to synthesize novel C-4 substituted retinoic acid analogs.

It is a further object of this invention that the synthesized C-4 retinoic acid analogs inhibit ATRA 4-hydroxylase. The terms "inhibit" and "inhibition" include total inhibition and less than total inhibition of ATRA 4-hydroxylase.

It is another object of this invention to use the novel C-4 substituted retinoic acid analogs to inhibit ATRA 4-hydroxylase.

It is another object of this invention to use the novel C-4 substituted retinoic acid analogs alone or in combination with other compounds, including retinoic acid, to treat cancer. It is another object of this invention to use the novel C-4 substituted retinoic acid analogs alone or in combination with other compounds to treat melanoma, leukemia, lymphoma, breast, prostate, ovarian, lung, or other types of cancers.

It is another object of this invention to use the novel C-4 substituted retinoic acid analogs alone or in combination with other compounds, including retinoic acid, to treat dermatologic diseases or dermatologic conditions. It is another object of this invention to use the novel C-4 substituted retinoic acid analogs alone or in combination with other compounds to treat acne, psoriasis, wrinkling, photoaged skin, and other dermatologic conditions or diseases.

It is an object of this invention to synthesis a retinoic acid analog with azole substituted at C-4. It is a further object of this invention to use the C-4 substituted azole retinoic acid analog to treat cancer. It is a further object of this invention to use the C-4 substituted azole retinoic acid analog to treat melanoma, leukemia, lymphoma, breast, prostate, ovarian, lung or other types of cancers. It is a further object of this invention to use the C-4 substituted azole retinoic acid analog to treat dermatological diseases and dermatological conditions. It is a further object of this invention to use the C-4 substituted azole retinoic acid analog to treat psoriasis, and dermatological conditions ranging from acne to photoaged skin to wrinkling.

It is an object of this invention to synthesis a retinoic acid analog with sulfur substituted at C-4. It is a further object of this invention to use the C-4 substituted sulfur retinoic acid analog to treat cancer. It is a further object of this invention to use the C-4 substituted sulfur retinoic acid analog to treat melanoma, leukermia, lymphoma, breast, prostate, ovarian, lung or other types of cancers. It is a further object of this invention to use the C-4 substituted sulfur retinoic acid analog to treat dermatological diseases and dermatological conditions. It is a further object of this invention to use the C-4 substituted sulfur retinoic acid analog to psoriasis, and dermatological conditions ranging from acne to photoaged skin to wrinkling.

It is an object of this invention to synthesis an retinoic acid analog with oxygen substituted at C-4. It is a further object of this invention to use the C-4 substituted oxygen retinoic acid analog to treat cancer. It is a further object of this invention to use the C-4 substituted oxygen retinoic acid analog to treat melanoma, leukemia, lymphoma, breast, prostate, ovarian, lung or other types of cancers. It is a further object of this invention to use the C-4 substituted oxygen retinoic acid analog to treat dermatological diseases and dermatological conditions. It is a further object of this invention to use the C-4 substituted oxygen retinoic acid analog to treat psoriasis, and dermatological conditions ranging from acne to photoaged skin to wrinkling.

It is an object of this invention to synthesis an retinoic acid analog with nitrogen substituted at C-4. It is a further object of this invention to use the C-4 substituted nitrogen retinoic acid analog to treat cancer. It is a further object of this invention to use the C-4 substituted nitrogen retinoic acid analog to treat melanoma, leukemia, lymphoma, breast, prostate, ovarian, lung or other types of cancers. It is a further object of this invention to use the C-4 substituted nitrogen retinoic acid analog to treat dermatological diseases and dermatological conditions. It is a further object of this invention to use the C-4 substituted nitrogen retinoic acid analog to treat psoriasis, and dermatological conditions ranging from acne to photoaged skin to wrinkling.

It is an object of this invention to synthesis a retinoic acid analog with pyridyl groups substituted at C-4. It is a further object of this invention to use the C-4 substituted pyridyl groups retinoic acid analog to treat cancer. It is a further object of this invention to use the C-4 substituted pyridyl groups retinoic acid analog to treat melanoma, leukemia, lymphoma, breast, prostate, ovarian, lung or other types of cancers. It is a further object of this invention to use the C-4 substituted pyridyl groups retinoic acid analog to treat dermatological diseases and dermatological conditions. It is a further object of this invention to use the C-4 substituted pyridyl groups retinoic acid analog to treat psoriasis, and dermatological conditions ranging from acne to photoaged skin to wrinkling.

Animals, including mammals and humans may be treated.

Preferably, the other compound used in combination with the novel C-4 substituted retinoic acid analog is ATRA.

DETAILED DESCRIPTION OF THE INVENTION

Figure 1:
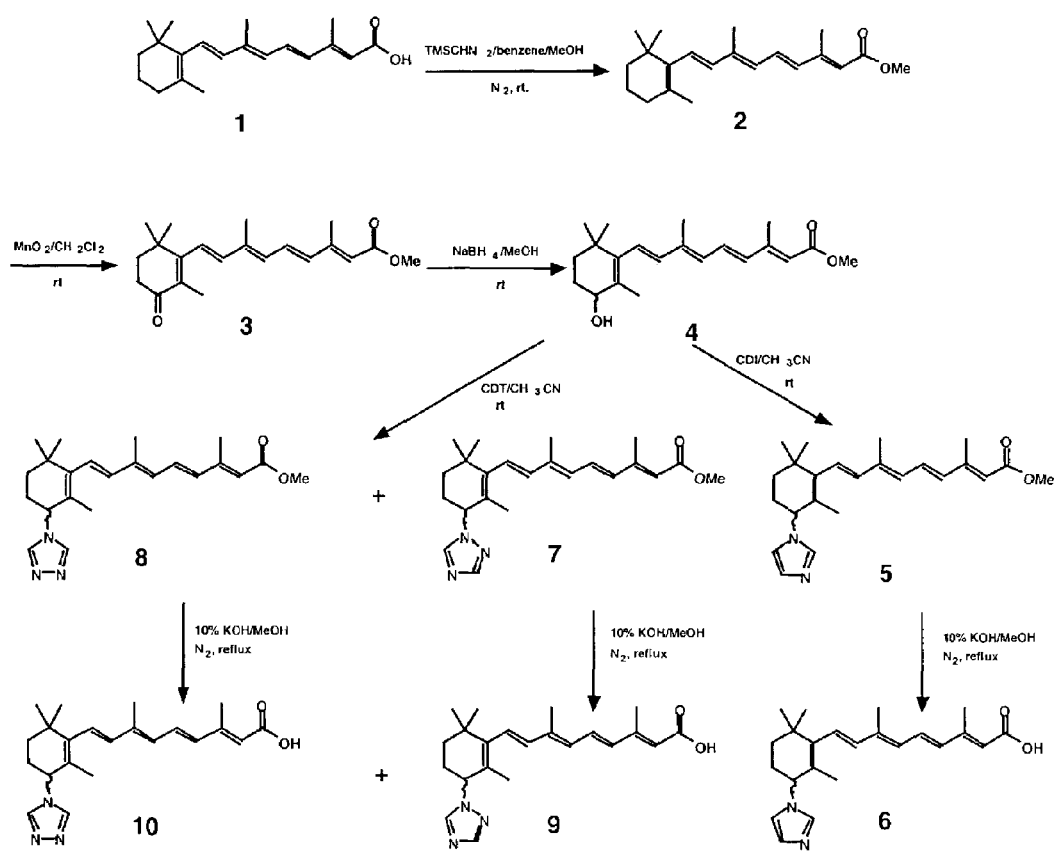
FIG. 1. Schematic pathway for synthesis of C-4 azole substituted ATRA analogs. TMSCHN$_2$ is an abbreviation for trimethylsilyldiazomethane; CDI is an abbreviation for carbonyldiimidazole; and CDT is an abbreviation for carbonylditriazole.

All-trans retinoic acid (ATRA) is a well-known and characterized compound. Its catabolic pathway involves ATRA 4-hydroxylase. The iron oxene species (Fe$^v$=O) of ATRA 4-hydroxylase is responsible for molecular oxygen activation and thus, the breakdown of ATRA. The Fe$^v$=O group of ATRA 4-hydroxylase has access to the C-4 of ATRA in that C-4 is within bonding distance of the activated oxygen. Substitution of suitable groups at the C-4 of ATRA will generate ATRA analogs which both react with the retinoid-binding site of the enzyme and interacts with the heme iron and/or the protein residue with high specificity. Substitutions of suitable groups can increase the inhibitory affects of the new compounds with K$_i$ values in the nanomolar range.

For ATRA analogs with C-4 substitutions with azole, sulfur, oxygen, or nitrogen, following binding at the active-site of the 4-hydroxylase enzyme, the lone pair of electrons coordinate to the prosthetic heme iron causing inhibition of the enzyme. Blockage of ATRA 4-hydroxylase activity increases the amount of ATRA.

In this invention, the "novel compounds" or "C-4 substituted retinoic acid analogs" are preferably ATRA and 13-CRA analogs with various moieties substituted for hydrogen at C-4 and also hydroxyl or various moieties substituted for hydroxyl at C-15. The chemical structure of C-4 substituted retinoic acid analogs is shown in Formula (I) below where R$_1$ is an azole group, a sulfur, oxygen, or nitrogen containing group, a pyridyl group, an ethinyl group, a cyclopropyl-amine group, an ester group, a cyano group, or R$_1$ forms, together with the C-4 carbon atom, an oxime, an oxirane or aziridine group and $R_2$ is a hydroxyl group, an aminophenol group, an ester group, or an azole group.

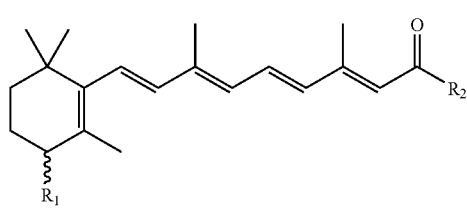

The compound may be used in a pharmaceutical composition. The pharmaceutical composition may be formulated for oral administration, parentral administration or for injectable administration.

In making the compositions of the present invention, the novel compound can be mixed with a pharmaceutically acceptable carrier or an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier, or medium for the novel compound. Thus, the compositions can be in the form of tablets, pills, powers, lozenges, sachets, cachets, elixirs, suspensions, emulsions, solutions, syrups, soft and hard gelatin capsules, and other orally ingestible formulations.

The pharmaceutical compositions may be in the form of a solution, suspension, tablet, capsule or the like, prepared according to methods well known in the art. It is also contemplated that administration of such compositions may be by the oral, injectable and/or parenteral routes depending upon the needs of the artisan. The novel compound can be administered by nasal or oral inhalation, oral ingestion, injection (intramuscular, intravenous, and intraperitoneal), transdermally, or other forms of administration.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include lubricating agents such as talc, magnesium stearate, and mineral oil; wetting agents; emulsifying and suspending agents; preserving agents such as methyl- and propyl-hydroxybenzoates, sweetening agents; and flavoring agents. The compositions of the present invention can also be formulated so as to provide quick, sustained or delayed release of the novel compound after administration to the patient by employing procedures known in the art.

The term "pharmaceutically acceptable carrier" refers to those components in the particular dosage form employed which are considered inert and are typically employed in the pharmaceutical arts to formulate a dosage form containing a particular active compound. This may include without limitation solids, liquids and gases, used to formulate the particular pharmaceutical product. Examples of carriers include diluents, flavoring agents, solubilizers, suspending agents, binders or tablet disintegrating agents, encapsulating materials, penetration enhancers, solvents, emollients, thickeners, dispersants, sustained release forms, such as matrices, transdermal delivery components, buffers, stabilizers, and the like. Each of these terms is understood by those of ordinary skill.

Aerosol formulations for use in this invention typically include propellants, such as a fluorinated alkane, surfactants and co-solvents and may be filled into aluminum or other conventional aerosol containers which are then closed by a suitable metering valve and pressurized with propellant, producing a metered dose inhaler. Aerosol preparations are typically suitable for nasal or oral inhalation, and may be in powder or solution form, in combination with a compressed gas, typically compressed air. Additionally, aerosols may be useful topically.

Generally, the amount of the novel compound used in the treatment methods is that amount which effectively achieves the desired therapeutic result in animals. Naturally, the dosages of the various novel compounds will vary somewhat depending upon the parent compound, rate of in vivo hydrolysis, etc. Those skilled in the art can determine the optimal dosing of the novel compound selected based on clinical experience and the treatment indication. Preferably the amount of the novel compound is 0.1 to 100 mg/kg of body weight, more preferably, 5 to 40 mg/kg.

Suitable solid carriers are known, e.g., magnesium carbonate, magnesium stearate, talc, lactose and the like. These carriers are typically used in oral tablets and capsules.

Suitable carriers for oral liquids include, e.g., water, ethanol, propylene glycol and others.

Topical preparations useful herein include creams, ointments, solutions, suspensions and the like. These may be formulated to enable one to apply the appropriate dosage topically to the affected area once daily, up to 3-4 times daily as appropriate. Topical sprays may be included herein as well.

Depending upon the particular compound selected, transdermal delivery may be an option, providing a relatively steady state delivery of the medication which is preferred in some circumstances. Transdermal delivery typically involves the use of a compound in solution, with an alcoholic vehicle, optionally a penetration enhancer, such as a surfactant and other optional ingredients. Matrix and reservoir type transdermal delivery systems are examples of suitable transdermal systems. Transdermal delivery differs from conventional topical treatment in that the dosage form delivers a systemic dose of medication to the patient.

The novel compound can also be converted into a pharmaceutically acceptable salt or pharmaceutically acceptable solvate or other physical forms (e.g., polymorphs by way of example only and not limitation) via known in the art field methods.

General Methods for Synthesis of Novel Compounds

Melting points (mp) are determined with a Fischer-Johns melting point apparatus and are uncorrected. Proton magnetic resonance spectra ($^1$H NMR) are recorded in $CDCl_3$ on a Mac NMR 5.3 300 MHz spectrometer (internal standard $Me_4Si$, ($\delta$=0), and high resolution mass spectra (HRMS) are determined on a Kratos Aspect Systems instrument, EI mode. Elemental analyses are performed by Chemisar Laboratories Inc., Guelph, Ontario, Canada. TLC is done on silica gel GHLF precoated plates (250 microns) purchased from Analtech, while flash column chromatography (FCC) is performed on silica gel (Merck grade 9385, 230-400 mesh, 60 Å) according to Still's method. (Still, W. C.; Kahn, M.; Mitra, A. Rapid Chromatographic Technique for Preparative Separation with Moderate Resolution. *J. Org. Chem.*, 43, 2923-2925, 1978). "Pet. ether" refers to light petroleum, bp 40-60° C. [11,12-$^3$H] All-trans-retinoic acid (ATRA, 51.8 Ci/mmol) is purchased from New England Nuclear Life Science Products, Inc., while unlabeled ATRA is purchased from Sigma-Aldrich Chemical Co., St. Louis, Mo. Liarozole fumarate is obtained from Janssen Pharmaceutica, Beerse, Belgium. (±)-4-Hydroxy-ATRA and 4-oxo-ATRA are prepared using a well-known technique (Samokyszyn, V. M.; Gall, W. E.; Zawada, G.; Freyaldenhoven, M. A.; Chen, G.; Mackenzie, P. I.; Tephly, T. R.; Radominska-Pandya, A. *4-Hydroxyretinoic Acid, a Novel Substrate for Human Liver Mcrosomal UDP-glucuronosyltransferase(s) and Recombinant UGT2B7. J. Biol. Chem.* 2000, 275, 6908-6914.)

C-4 Azole Substituted ATRA Analogs

The pathway for synthesis of C-4 azole substituted ATRA analogs is shown in FIG. 1. The starting point of the synthesis is ATRA, 1. Methyl retinoate, 2, is readily prepared in quantitative yield from ATRA, 1, by reaction with trimethylsilyl diazomethane (TMSCHN$_2$) using a well-known technique (Hashimoto, N.; Aoyoma, T.; Shioiri, T. *New Methods and Reagents in Organic Synthesis, A simple Efficient Preparation of Methyl Esters with Trimethylsilyl-diazomethane (TMSCHN$_2$) and Its Application to Gas Chromatographic Analysis of Fatty Acids, Chem. Pharm. Bull.,* 29. 1475-1478, 1981). Then methyl retinoate, 2, (1.04 g, 3.3 mmol) dissolved in dry CH$_2$Cl$_2$ (100 mL) is treated with excess activated MnO$_2$ (20 g, ex Fluka), and the reaction mixture is stirred at room temperature for 48 hours. The MnO$_2$ is removed by filtration, the filtrate is concentrated to afford an orange viscous oil which is purified by FCC [pet. ether/EtOAc, (8:1)] to give starting material (2.2 g) and 4-oxo-all-trans-methyl retinoate, 3, (0.65 g, 60%) as a viscous oil. 4-oxo-all-trans-methyl retinoate, 3, is crystallized from pet. ether at room temperature, mp 94-95° C. $^1$H NMR δ 1.19 (6H, s, 16- and 17-Mes), 1.86 (3H, s, 18-Me), 2.04 (3H, s, 19-Me), 2.37 (3H, s, 20-Me), 3.72 (3H, s, OMe), 5.82 (1H, s, 14-H), 6.30 (4H, m, 7-, 8-, 10- and 12-Hs), 6.98 (1H, t, J=11.4 Hz, 11-H). HRMS calculated for C$_{21}$H$_{28}$O$_3$, 328.2038. Found: 328.2030.

The next step is to synthesize (±)-4-hydroxy-all-trans-methyl retinoate, 4. To a stirred solution of 4-oxo-all-trans-methyl retinoate, 3, (500 mg, 1.52 mmol) in dry MeOH (15 mL) at room temperature is added NaBH$_4$ (53 mg, 1.40 mmol). After 30 minutes, the reaction is quenched with H$_2$O and concentrated. The residue is diluted with EtOAc, washed with H$_2$O, brine, dried (Na$_2$SO$_4$), and concentrated to give a yellow semi-solid which crystallized following tituration with hexane to give (±)-4-hydroxy-all-trans-methyl retinoate, 4, yellow crystals (452 mg, 91%), mp 102-104° C. $^1$H NMR δ 1.02, 1.05 (6H, 2s, 16- and 17-Mes), 1.84 (3H, s, 18-Me), 2.00 (3H, s, 19-Me), 2.36 (3H, s, 20-Me), 3.72, (3H, s, OMe), 4.00 (1H, brs, 4-H), 5.79 (1H, s, 14-H), 6.20 (4H, m, 7-, 8-, 10- and 12-Hs), 6.99 (1H, t, J=11.7 Hz, 11-H). Anal. calculated for C$_{21}$H$_{30}$O$_3$: C, 76.31; H, 9.16. Found: C, 76.39; H, 9.10. HRMS calculated for C$_{21}$H$_{30}$O$_3$, 330.2195. Found: 330.2191.

The next step is to synthesis (±)-4-(1H-imidazol-1-yl)-methyl retinoate, 5. A solution of 4-hydroxy-all-trans-methyl retinoate, 4, (300 mg, 0.9090 mmol) and carbonyldi-imidazole (CDI, 195 mg, 1.2025 mmol) in dry CH$_3$CN (5.0 mL) is stirred at room temperature for 10 minutes. The reaction mixture is diluted with water (20 mL) and extracted with 10% MeOH in CH$_3$Cl (10 mL×3). The combined extract is washed with brine (10 mL×2), dried (Na$_2$SO$_4$) and evaporated to give a viscous yellow oil (350 mg). This is purified by FCC [CH$_2$Cl$_2$/EtOAc/Et$_3$N, (7:3:0.3)] to give (±)-4-(1H-imidazol-1-yl)-methyl retinoate, 5, as a yellow semi-solid (311 mg, 90%): $^1$H NMR δ 1.09 and 1.12 (6H, 2s, 16- and 17-Hs), 1.60 (3H, s, 18-Me), 2.02 (3H, s, 19-Me), 2.36 (3H, 3, 20-Me), 3.72 (3H, s, OMe), 4.53 (1H, s, 4-H), 5.80 (1H, s, 14-H), 6.25 (4H, m, 7-, 8-, 10- and 12-Hs), 6.91 (1H, s, 4'-H), 6.98 (1H, t, J=14.7 Hz, 11-H), 7.07 (1H, s, 5$^1$-H), 7.50 (1H, s, 2$^1$-H). HRMS calculated for C$_{24}$H$_{32}$O$_2$N$_2$, 380.5331. Found: 380.5334.

The next step involves synthesis of (±)-4-(1H-imidazole-1-yl)retinoic acid, 6 (also referred to as "VN/14-1RA"). A solution of (±)-4-(1H-imidazol-1-yl)-methyl retinoate, 5, (270 mg, 0.7077 mmol) in 12 mL of 1M KOH in a 1:9 mixture of water and MeOH is diluted with MeOH (14 mL), and is followed by refluxing under N$_2$ for 2 hour. The reaction mixture is concentrated to approximately 10 mL, diluted with cold water (25 mL) and is acidified with a few drops of 6N HCl. The resulting yellow precipitate is filtered, washed and dried to give pure (±)-4-(1H-imidazole-1-yl) retinoic acid, 6, as a yellow solid (225 mg, 86.6%): mp 128-130° C., $^1$H NMR δ 1.13 (6H, s, 16- and 17-Hs), 1.67 (3H, s, 18-Me), 2.02 (3H, s, 19-Me), 2.32 (3H, s, 20-Me), 4.84 (1H, s, 4-H), 5.85 (1H, s, 14-H), 6.21 (3H, s, 8-, 10- and 12-Hs), 6.33 (1H, d, J=15.0 Hz, 8-H), 7.00 (1H, t, J=14.0 Hz, 11-H), 7.16 (1H, s, 4'-H), 7.26 (1H, s, 5$^1$-H), 7.46 (1H, s, 2$^1$-H), 8.75 (1H, brs, —COOH). Anal. calculated for C$_{23}$H$_{30}$O$_2$N$_2$: C, 75.38; H, 8.25; N, 7.64. Found: C, 75.72; H, 8.65; N, 7.67. HRMS calculated for C$_{23}$H$_{30}$O$_2$N$_2$, 366.3061. Found: 366.3056.

To synthesize triazole groups at C-4, one follows an alternate pathway. Beginning with (±)-4-hydroxy-all-trans-methyl retinoate, 4, a solution of (±)-4-hydroxy-all-trans-methyl retinoate, 4, (270 mg, 0.8182 mmol) and N,N$^1$-carbonyldi(1,2,4-triazole) (CDT) (187.1 mg, 1.1340 mmol) in dry CH$_3$CN (4.5 mL) is stirred at room temperature for 10 minutes. The reaction mixture is diluted with water (20 mL) as was processed as described above for (±)-4-(1H-imidazol-1-yl)-methyl retinoate, 5, above to give a yellow solid (310 mg). Analytical TLC [CH$_2$Cl$_2$/EtOH, (20:1)] reveals the presence of two compounds, both more polar that (±)-4-hydroxy-all-trans-methyl retinoate, 4. This crude product is subjected to FCC and on elution with CH$_2$Cl$_2$/EtOH (35:1), gives (±)-4-(1H-1,2,4-triazol-1-yl)methyl retinoate, 7, (177 mg, 57%): mp. 105-108° C.; $^1$H NMR δ 1.10 and 1.13 (6H, 2s, 16- and 17-Mes), 1.63 (3H, s, 18-Me), 2.02 (3H, s, 19-Me), 2.36 (3H, s, 20-Me), 3.72 (3H, s, OMe), 4.82 (1H, s, 4-H), 5.80 (1H, s, 14-H), 6.30 (4H, m, 7-, 8-, 10- and 12-Hs), 6.99 (1H, t, J=14.1 Hz, 11-H), 7.99 (1H, s, 3$^1$-H), 8.02 (1H, s, 5$^1$-H). Anal. calculated for C$_{23}$H$_{31}$O$_2$N$_3$: C, 72.41; H, 8.19; N, 11.01. Found: C, 72.45; H, 8.15; N, 10.97. HRMS calculated for C$_{23}$H$_{31}$O$_2$N$_3$, 381.5208. Found: 381.5211.

Further elution with CH$_2$Cl$_2$/EtOH (20:1) affords (±)-4-(4H-1,2,4-triazole-1-yl)methyl retinoate, 8, (89 mg, 28.5%): mp 62-65° C.; $^1$H-NMR δ 1.10 and 1.13 (6H, 2s, 16- and 17-Mes), 1.64 (3H, s, 18-Me), 2.02 (3H, s, 19-Me), 2.36 (3H, s, 20-Me), 3.72 (3H, s, OMe), 4.64 (1H, s, 4-H), 5.81 (1H, s, 14-H), 6.25 (4H, m, 7-, 8-, 10- and 12-Hs), 6.98 (1H, t, J=14.4 Hz, 11-H), 8.15 (2H, s, 3$^1$- and 5$^1$-H). Anal. calculated for C$_{23}$H$_{31}$O$_2$N$_3$: C, 72.41; H, 8.19; N, 11.01. Found: C, 72.55; H, 8.10; N, 11.00. HRMS calculated for C$_{23}$H$_{31}$O$_2$N$_3$, 381.5208. Found: 381.5213.

To synthesize (±)-4-(1H-1,2,4-triazol-1-yl)retinoic acid, 9, (also referred to as "VN/16-1RA"), use the method that describes the synthesis for VN/14-1RA (above) but use (±)-4-(1H-1,2,4-triazol-1-yl)methyl retinoate, 7, (285 mg, 0.7470 mmol) to give VN/16-1RA (247 mg, 90%): mp 95-97° C.; $^1$H-NMR δ 1.10 and 1.13 (6H, 2s, 16- and 17-Mes), 1.65 (3H, s, 18-Me), 2.03 (3H, s, 19-Me), 2.36 (3H, s, 20-Me), 4.86 (1H, s, 4-H), 5.84 (1H, s, 14-H), 6.32 (4H, m, 7-, 8-, 10- and 12-Hs), 7.01 (1H, t, J=14.5 Hz, 11-H), 8.10 (1H, s, 3$^1$-H), 8.31 (1H, s, 5$^1$-H). Anal. calculated for $C_{22}H_{29}O_2N_3$: C, 71.90; H, 7.95; N, 11.43. Found: C, 71.70; H, 8.11; N, 11.55. HRMS calculated for $C_{22}H_{29}O_2N_3$, 367.4938. Found: 367.4935.

To synthesize (±)-4-(4H-1,2,4-triazol-1-yl)retinoic acid, 10, (also referred to as "VN/17-1RA") use the method that describes the synthesis for VN/14-1RA (above) but use (±)-4-(4H-1,2,4-triazole-1-yl)methyl retinoate, 8, (134 mg, 0.3512 mmol) to give VN/17-1RA (110 mg, 85%): mp 105-108° C.; $^1$H-NMR δ 1.11 and 1.14 (6H, 2s, 16- and 17-Mes), 1.65 (3H, s, 18-Me), 2.03 (3H, s, 19-Me), 2.37 (3H, s, 20-Me), 4.78 (1H, s, 4-H), 5.85 (1H, s, 14-H), 6.19 (4H, m, 7-, 8-, 10- and 12-Hs), 7.01 (1H, t, J=14.2 Hz, 11-H), 8.46 (2H, s, 3'- and 5$^1$H). Anal. calculated for $C_{22}H_{29}O_2N_3$: C, 71.90; H, 7.95; N, 11.43. Found: C, 71.90; H, 7.79; N, 11.30. HRMS calculated for $C_{22}H_{29}O_2N_3$, 367.4938. Found: 367.4939.

C-4 Sulfur Substituted ATRA Analogs

Figure 2:
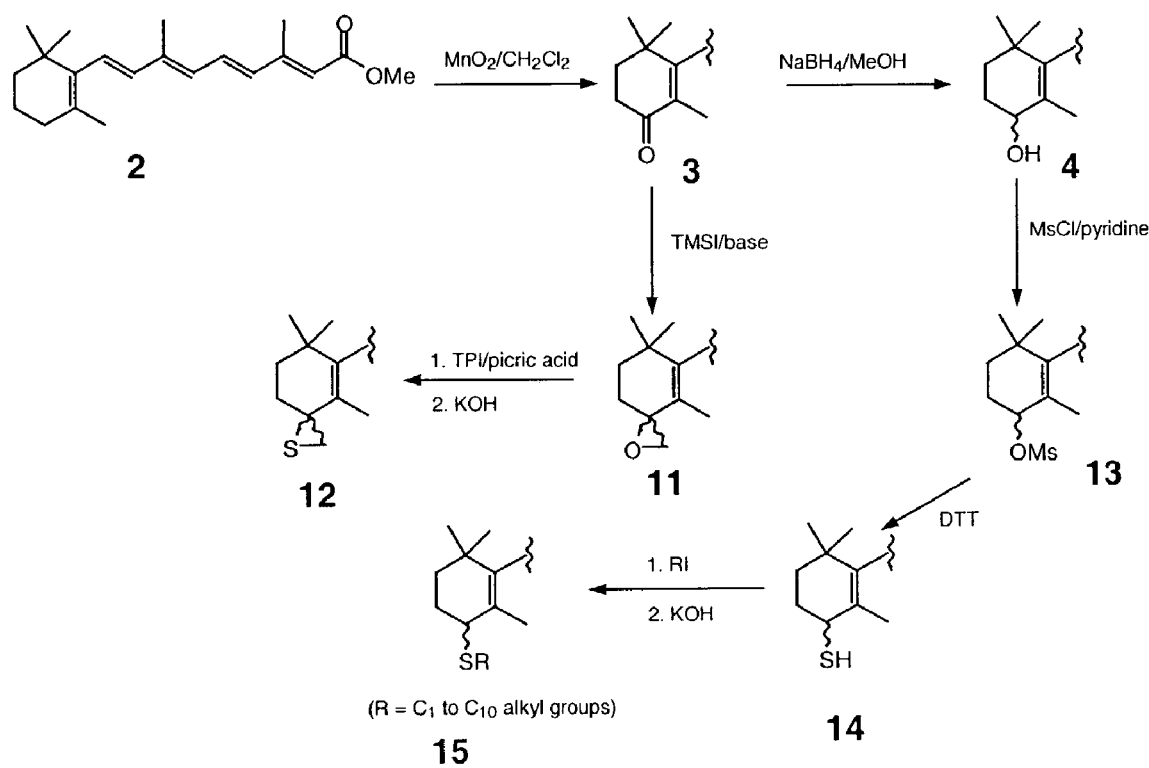
FIG. 2. Schematic pathway for synthesis of C-4 sulfur substituted ATRA analogs. TMSI is an abbreviation for trimethylsulfonium iodide, TPS is an abbreviation for triphenylphosphine sulfide, and DDT is an abbreviation for dithiothreitol.

FIG. 2 shows the schematic pathway for synthesis of C-4 sulfur substituted ATRA analogs. The C-4 sulfur substituted ATRA analogs include 4-thiirane 12, 4-thiol 14, and 4-alkylthio derivatives 15. Methyl retinoate 2 is transformed into 4-oxirane 11 via 4-oxomethylretinoate 3. Treatment of 4-oxirane 11 with trimethylsulfonium iodide (TPI) in picric acid followed by hydrolysis affords 4-thiirane 12. 4-thiol 14 is prepared from 4-mesylate 13 by treatment with dithiothreitol (DTT). Treatment of 4-thiol 14 with various alkyl halides affords the desired 4-alkyl derivatives 15.

C-4 Oxygen Substituted ATRA Analogs

Figure 3:
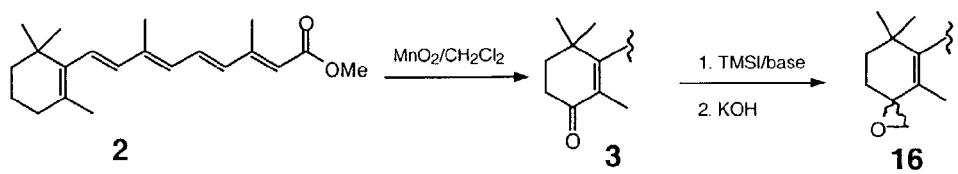
FIG. 3. Schematic pathway for synthesis of C-4 oxygen substituted ATRA analogs.

FIG. 3 shows the synthesis pathway for C-4 oxygen substituted ATRA analogs. 4-oxirane 16 is synthesized from the 4-oxo compound 3 by treatment with TMSI followed by hydrolysis in methanolic KOH as shown in FIG. 3.

C-4 Nitrogen Substituted ATRA Analogs

Figure 4:
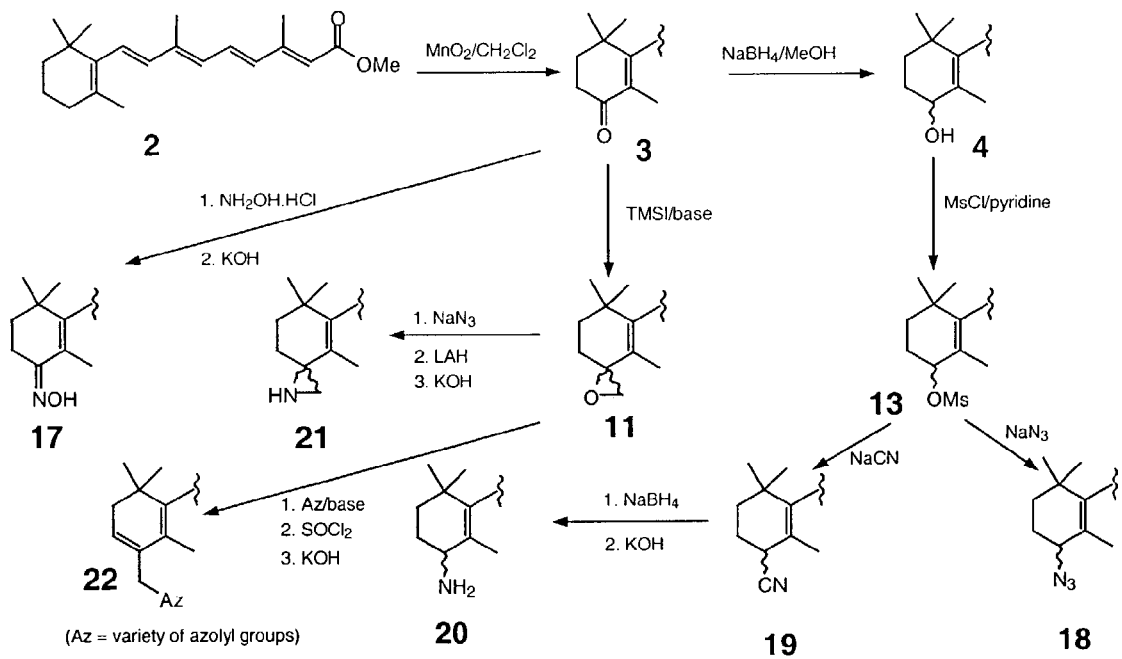
FIG. 4. Schematic pathway for synthesis of C-4 nitrogen substituted ATRA analogs.

FIG. 4 shows the synthesis pathway for C-4 nitrogen substituted ATRA analogs such as 4-oxime 17, 4-azido 18, 4-cyano 19, 4-amine 20, 4-aziridine 21, and 4-allylic azoles 22. Treatment of 4-oxo methylretinoate 3 with hydroxylamine hydrochloride followed by hydrolysis yields 4-oxime 17. Treatment of 4-mesylate 13 with either $NaN_3$ or NaCN followed by hydrolysis yields 4-azido 18 and 4-cyano 19, respectively. $NaBH_4$ reduction of 4-cyano 19 yields 4-amine 20. Reaction of 4-oxirane 11 sequentially with $NaN_3$, LAH and methanolic KOH yields 4-allylic azoles 22.

C-4 Pyridyl ATRA Analogs

Figure 5:
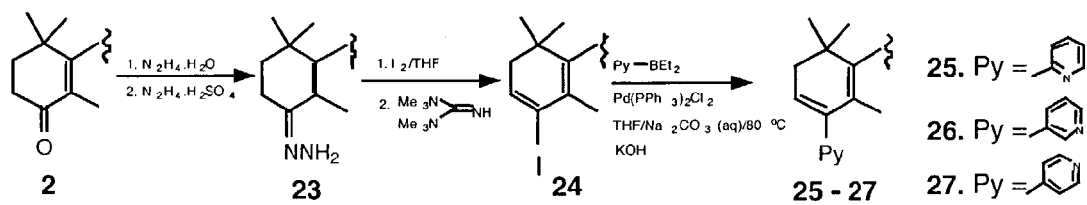
FIG. 5. Schematic pathway for synthesis of C-4 pyridyl substituted ATRA analogs.

Introduction of various pyridyl groups at C-4 yields potent inhibitors of ATRA 4-hydroxylase. These C-4 substituted pyridyl ATRA analogs interact with ATRA 4-hydroxylase's active site. The synthesis pathway of these C-4 substituted pyridyl ATRA analogs are shown in FIG. 5. Thus 4-oxo methylretinoate, 2, is transformed to the key intermediate vinyl iodide, 24, via the hydrazone, 23. Palladium catalyzed cross-coupling reaction of 24 with different diethyl(-pyridyl)borane reagents affords the desired C-4 substituted pyridyl ATRA analogs, 25, 26 and 27.

C-4 Alkylating Agent ATRA Analogs

Figure 6:
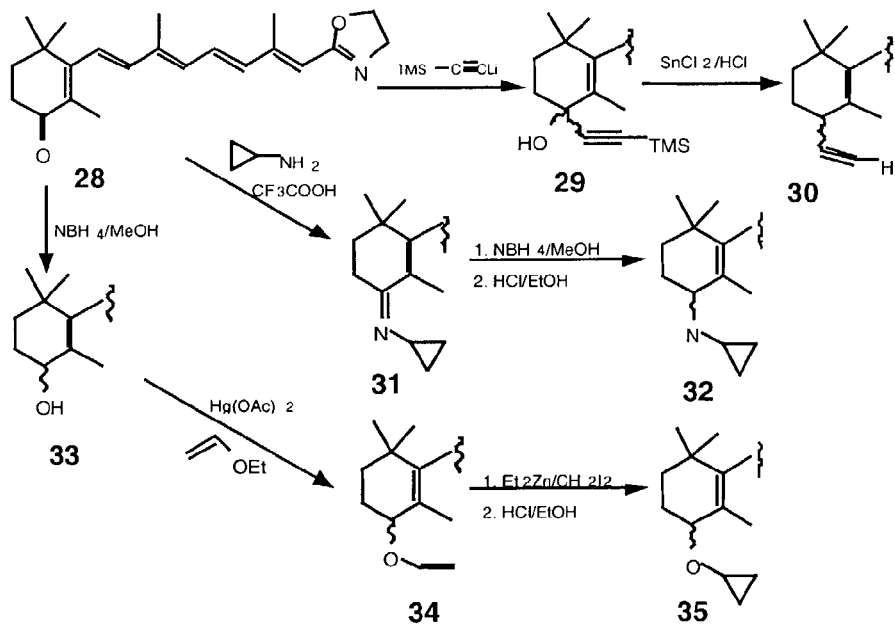
FIG. 6. Schematic pathway for synthesis of C-4 substituted ATRA analogs that are mechanism-based inhibitors.

C-4 alkylating agent ATRA analogs are mechanism based inhibitors which are substrate analogs of ATRA. These C-4 substituted ATRA analogs contain a latent electrophilic group which is activated by ATRA 4-hydroxylase resulting in irreversible enzyme inactivation because of covalent modification of the active site of ATRA 4-hydroxylase. FIG. 6 shows the schematic pathway for synthesis of C-4 substituted ATRA analogs that are mechanism-based inhibitors. The alkylating agents are C-4 substituted ATRA analogs: acetylinic ATRA, 30, cyclopropyl-amine ATRA, 32, and cyclopropyl-ether-ATRA, 35. Acetylinic ATRA, 30, undergoes oxygen insertion to yield the highly reactive oxirene species which covalently binds to the prosthetic heme via its α-ketocarbene tautomer. Similarly, cyclopropyl-amine ATRA, 32, and cyclopropyl-ether-ATRA, 35, each inhibit ATRA 4-hydroxylase following one-electron enzymatic oxidation.

Protection of the carboxylic acid moiety of 4-keto-ATRA as the 2-alkyl-1,3-oxazolidie, 28, according to established procedure (Schow SR, Bloom JD, Thompson A S, Winzenberg K N and Smith III A B (1986) Milbemycin-Avemictic studies. 5. Total synthesis of milbemycin 3 and its C(12) epimers. *J Am Chem Soc* 108: 2662-2674.) followed by treatment with lithium acetylide (Mauvais A, Burger A, Roussel P J, Hetru C and Luu B (1994) Acetylenic inhibitors of C-22 hydroxylase of ecdysone biosynthesis. *Bioorg Chem* 22: 36-50.) yields 4-hydroxy, 4-trimethylsilylacetylene 29. Reduction of the latter with $SnCl_2$ in HCl yields acetylinic ATRA, 30 (FIG. 6).

The cyclopropyl compounds may also be synthesized from 2-alkyl-1,3-oxazolidie, 28, as shown in FIG. 6. Condensation of 2-alkyl-1,3-oxazolidie, 28, with cyclopropylamine, followed by reduction of the resulting imine with $NaBH_4$ gives cyclopropyl-amine ATRA, 32. The cyclopropyl ether ATRA, 35, is prepared by vinylation and subsequent cyclopropanation.

Synthesis of Retinamides

Figure 13:
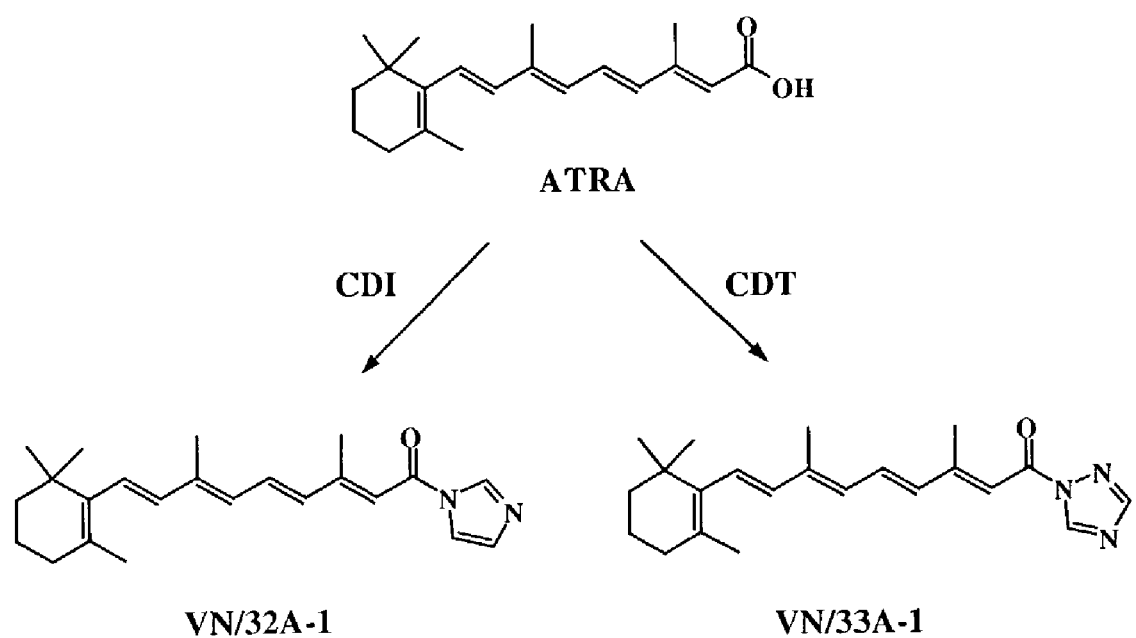
FIG. 13: Schematic pathway for the Synthesis of Retinamides; CDI is an abbreviation for carbonyldiimidazole; and CDT is an abbreviation for carbonylditriazole.

Retinamides may used to form C-4 substituted retinamides. For example, all-trans-retinoyl-imidazole (VN/32A-1) and all-trans-retinoyl-1,2,4-triazole (VN/33A-1) may be synthesized in quantitative yields by treatment of all-trans-retinoic acid with 1.3 equivalents each of carbonyldiimidazole (CDI) and carbonylditriazole (CDT), respectively as outlined in FIG. 13. The retinamides may be further treated as above to form C-4 substituted retinamides.

Synthesis of (±)-4-(1H-imidazol-1-yl)-13-cis-methylretinoate (VN/65-4) and (±)-4-(1H-imidazol-1-yl)-13-cis-retinoic acid (VN/67-1), (±)-4-(1H-imidazol-1-yl)-13-cis-retinoyl-imidazole (VN/68-1), (±)-4-(1H-imidazol-1-yl)- N-(4$^1$-hydroxyphenol)13-cis-retinamide (VN/69-1)

Figure 14:
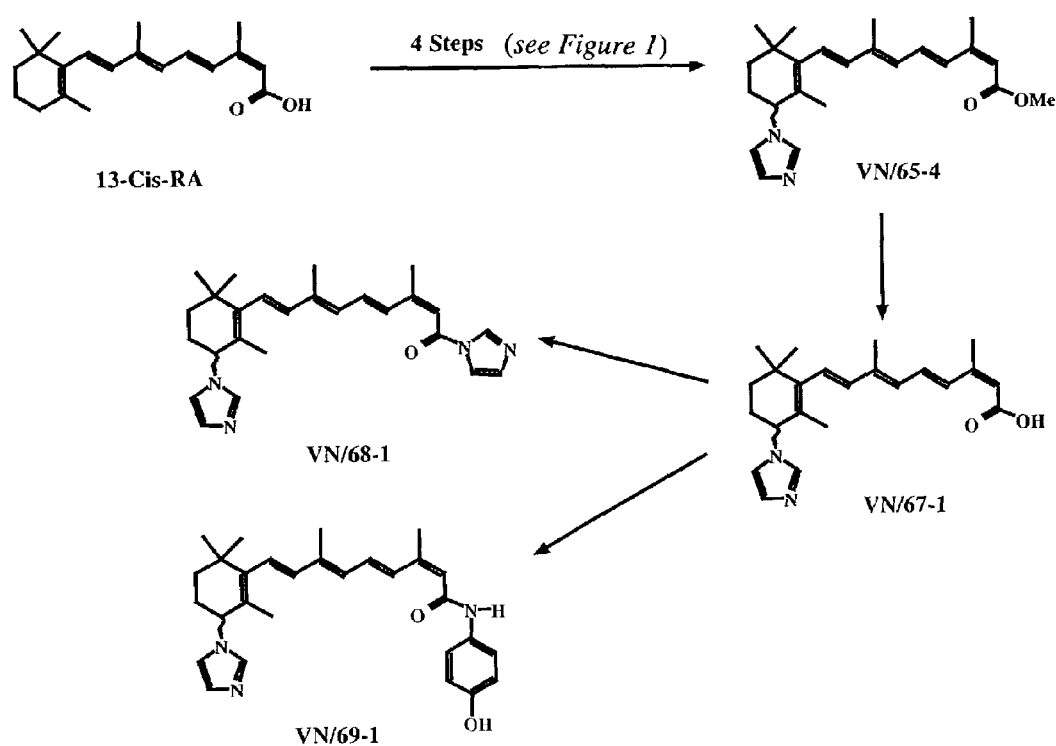
FIG. 14: Schematic pathway for the synthesis of (±)-4-(1H-imidazol-1-yl)-13-cis-methylretinoate (VN/65-4) and (±)-4-(1H-imidazol-1-yl)-13-cis-retinoic acid (VN/67-1), (±)-4-(1H-imidazol-t-yl)-13-cis-retinoyl-imidazole (VN/68-1), (±)-4-(1H-imidazol-1-yl)-N-(4$^1$-hydroxyphenol)13-cis-retinamide (VN/69-1).

VN/65-4 was synthesized from commercially available 13-cis-retinoic acid following the procedure described for the synthesis of VN/12-1. Hydrolysis of VN/65-4 in methanolic KOH yielded the corresponding acid, VN/67-1. Treatment of VN/67-1 with CDI in $CH_3CN$ gave the corresponding retinoylimidazole (VN/68-1). VN/69-1 was synthesized by coupling VN/67-1 with 4-aminophenol by the active ester method using dicyclohexylcarbodiimide (DCC) and 1-hydroxybenzonitrile (HOBT) in dimethylformamide (DMF) (FIG. 14).

Synthesis of (±)-4-(1H-imidazol-1-yl),N-(4$^1$-hydroxyphenol)retinamide (VN/66-1)

Figure 15:
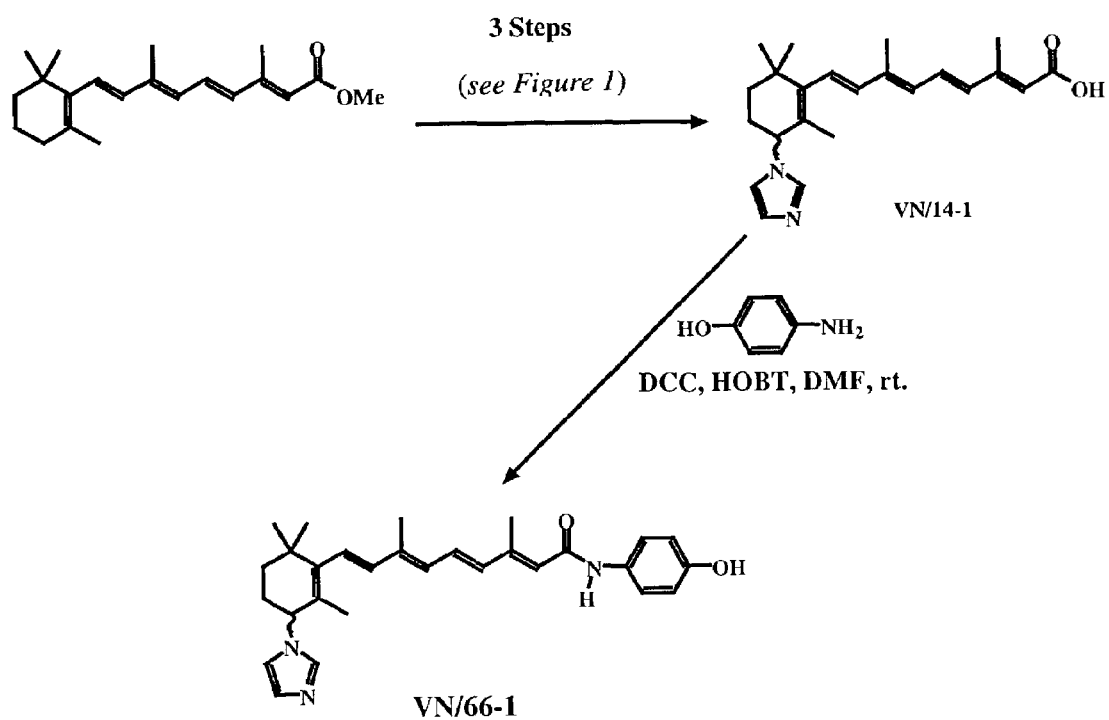
FIG. 15: Schematic pathway for the Synthesis of (±)-4-(1H-imidazol-1-yl), N-(4'-hydroxyphenyl)retinamide (VN/66-1); DCC is an abbreviation for dicyclohexylcarbodiimide; HOBT is an abbreviation for 1-hydroxybenzonitrile; and DMF is an abbreviation for dimethylformamide.

VN/66-1 was synthesized by coupling VN/14-1 (obtainable as shown in FIG. 1) with 4-aminophenol by the active ester method using dicyclohexylcarbodiimide (DCC) and 1-hydroxybenzonitrile (HOBT) in dimethylformamide (DMF) (FIG. 15).

ATRA 4-hydroxylase Inhibition

C-4 substituted ATRA analogs inhibit ATRA 4-hydroxylase. Two types of assays demonstrate this inhibitory effect. One assay uses hamster liver microsomes. The other type of assay uses COS-1 cells transfected with hP450RAI, human ATRA 4-hydroxylase. The reason for the two types of assays is that hamster liver microsomes have several different cytochrome P450 enzymes, and one needs to see that the novel compounds specifically inhibit ATRA 4-hydroxylase.

Hamster Liver Microsome Assay Method

Washed hamster liver microsomes were prepared as follows: Livers are removed from sacrificed animals, rinsed in ice-cold 0.9% NaCl solution and homogenized in a 3-fold volume of 0.25 M sucrose-0.05 M Tris-HCl (pH 7.4) using a blender. Microsomes are isolated by differential centrifugation (10,000× g, 20 minutes; 100,000× g, 60 minutes; 4° C.) using a well-known technique (Van Wauwe, J.; Van Nyen, G.; Coene, M-C.; Stoppie, P.; Cols, W.; Goossens, J, Borghgraef, P.; Janssen, P A J, *Liarozole, an Inhibitor of Retinoic Acid Metabolism, Exerts Retinoid-Mimetic Effects, In Vivo. J. Pharmacol. Expt. Ther.* 261, 773-779, 1992). The microsomes are suspended in PBS buffer (pH 7.4), in 1 ml aliquots and stored at −70° C. until required.

The standard reaction mixture (total of 400 μl) is composed of assay buffer, 140 μl; microsomes, 100 μl (500 mg protein); NADPH, 100 μl (20 nM); and a C-4 substituted ATRA analog dissolved in DMSO, 40 μl. After a 3 minute preincubation at 37° C., the reaction is initiated by addition of 20 μl of [11,12-$^3$H]-ATRA (20 μCi/ml). The incubation is carried out for 30 minutes under oxygen with shaking in a water bath at 37° C. The reaction is stopped by acidification with 0.1 ml formic acid, and the samples are extracted (×2) with EtOAc (2 ml) containing 0.05% butylated hydroxyanisole. The combined organic extracts are evaporated in vacuo, dissolved in 200 μl of the mobile phase for HPLC. An aliquot is analyzed for tritium content by liquid scintillation spectrometry. Usually, >95% of the added radioactivity is recovered. Most of the samples (150 μl) are analyzed on a 10 (m $C_{18}$ Bondapak column (3.9×300 mm, Millipore), eluted with a multi-linear gradient solvent system: i, MeOH—$H_2$O—HCOOH (60:40:0.05) containing 10 mM ammonium acetate (100 (0%) and ii, MeOH (0 (100%) at 2 ml/min. The radioactivity is measured by an on-line radiodetector. The $R_{ts}$ of ATRA, 4-hydroxy-ATRA and 4-oxo-ATRA are determined by UV absorbance at 350 nm in separate cuvettes. Typically, 80±5% of [11, 12-$^3$H]ATRA is converted into the metabolites.

The C-4 substituted ATRA analogs are tested at two concentrations, 500 and 1000 nM. $IC_{50}$ and $K_i$ values are determined.

hP450RAI-Transfected COS-1 Cells Method

An hP450RAI expression vector is transfected into COS-1 according to standard protocols, and the assay is conducted using standard protocols (White J A, Guo Y-D, Baetz K, Beckett-Jones B, Bonasoro J. Hsu K E, Dilworth F J, Jones G and Petkovich M, *Identification of the retinoic acid-inducible all-trans-retinoic acid 4-hydroxylase,* J Biol Chem 271: 29922-29927 1996; White J A, Beckett-Jones B, Guo Y-D, Dilworth F J, Bonasoro J. Jones G and Petkovich M, *Cloning of the human retinoic acid-metabolizing enzymes (hP450RAI) identifies a novel family of cytochromes P450(CYP26),* J Biol Chem 272: 18538-18541, 1997). Briefly, COS-1 cells are transfected with 3 g of hP450RAI in pTLI or the empty control pTLI together with 1 g of ferridoxin and ferridoxin reductase expression vectors. Media from transfected cells is incubated with 575 pM [11, 12-$^3$H]ATRA for 24 hours, and reactions are terminated by acidification with 0.1% acetic acid. Metabolism of [11, 12-$^3$H]ATRA to polar metabolites is quantified as described above, and the novel compounds are assessed for their inhibitory potencies.

Effects of Compounds on in vitro Metabolism of ATRA

Figure 7:
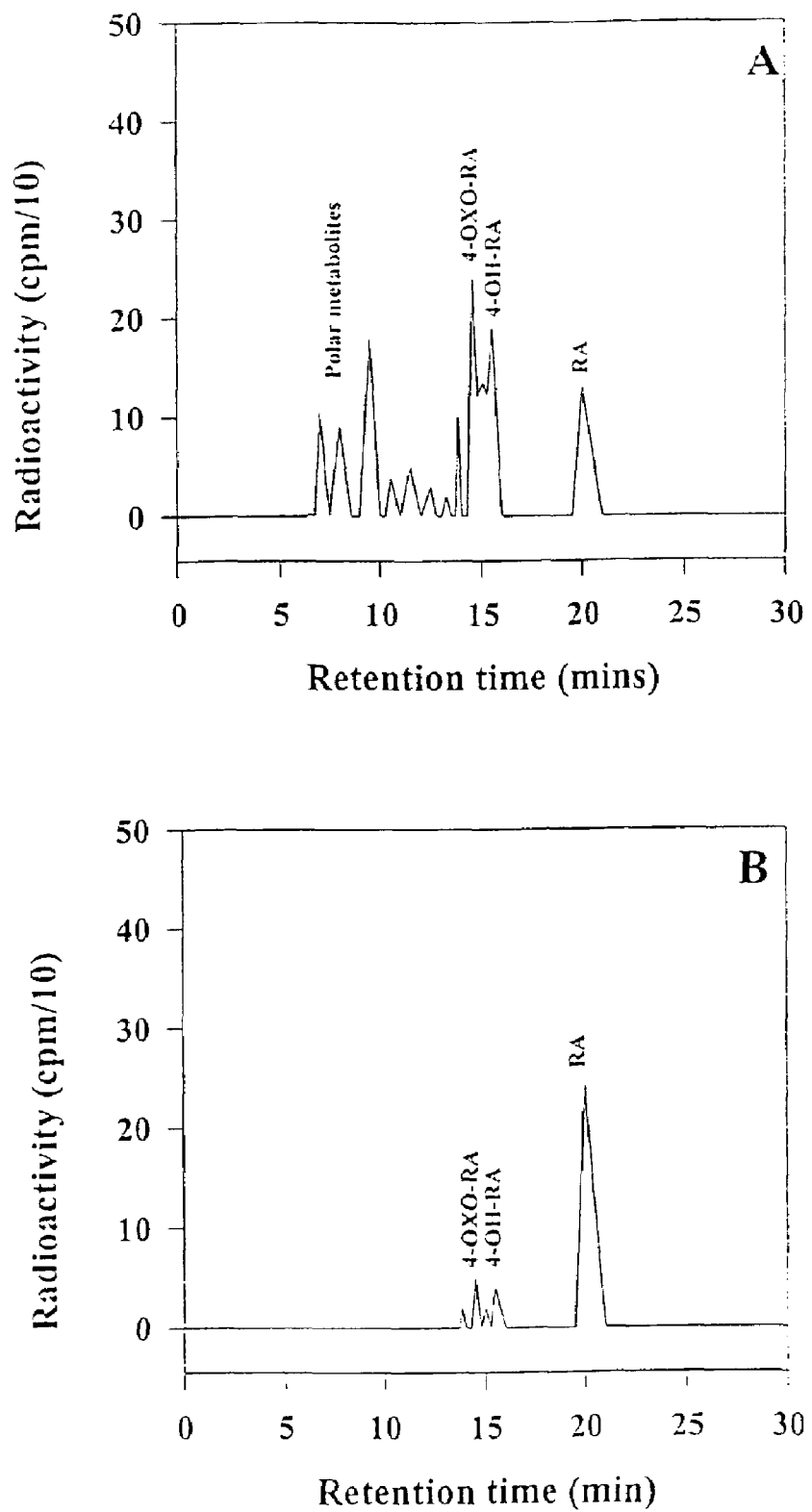
FIGS. 7A-7B. Inhibition of ATRA metabolism in hamster liver microsomes in absence of VN/14-1RA (FIG. 7A) and in the presence of has 1 µM of VN/14-1RA (FIG. 7B).

Incubation of [11,12-$^3$H]ATRA with hamster liver microsomes as described above results in the formation of polar metabolites, including 4-hydroxy-ATRA and 4-oxo-ATRA (see FIG. 7A). However, VN/14-1RA (1 μM) significantly suppressed the microsomal conversion of ATRA to polar metabolites (see FIG. 7B). VN/14-1RA inhibits cytochrome P450-dependent metabolism of ATRA.

Dose-response experiments were used to determine the $IC_{50}$ values of our inhibitors and the results are presented in Table 2A and B below. Table 2A represents initial testing. Table 2B represents repeated testing of some of the compounds in Table 2A and testing on additional compounds. For comparison, the $IC_{50}$ values of liarozole and ketoconazole (known inhibitors of ATRA 4-hydroxylase) were also determined.

TABLE 2A

| Compounds | $IC_{50}$ Value (nM) |
| --- | --- |
| VN/14-1RA | 100 ± 1.0 |
| VN/16-1RA | 880 ± 8.0 |
| VN/16-1RA methyl ester | 680 ± 3.0 |
| VN/17-1RA | 1,620 ± 8.0 |
| Liarozole | 6,000 ± 30.0 |
| keto | 34,000 ± 170.0 |

TABLE 2B

| Inhibition of ATRA 4-Hydroxylase | |
| --- | --- |
| Compound | $IC_{50}$ Value (nM) |
| VN/12-1 | 0.05 ± 0.003 |
| VN/13-1 | 1.00 ± 0.050 |
| VN/13-2 | 10.00 ± 0.300 |
| VN/14-1 | 1.20 ± 0.072 |
| VN/16-1 | 5.00 = 0.250 |
| VN/17-1 | 25.00 ± 0.500 |
| VN/50A-1 | 0.025 ± 0.001 |
| VN/51A-1 | 10.00 ± 0.400 |
| VN/65-4 | 20.00 ± 0.550 |
| VN/66-1 | 5.00 ± 0.300 |
| For comparison | |
| Liarozole | 6000.00 ± 30.00 |
| Ketoconazole | 34000.00 ± 170 |

The compounds of the present invention are highly potent inhibitors of ATRA metabolism and they are also remarkably more potent than liarozole. From these results it is believed that the nature of the azole moiety is important in determining affinity for the enzyme and it is also believed that the corresponding methyl esters and amides are more potent than the corresponding free acids. The most active compound, VN/50A-1 with an $IC_{50}$ value of 0.025 nM is remarkably 240,000-fold more potent than liarozole ($IC_{50}$=6,000 nM).

The selectivity of the compounds of the present invention towards ATRA-4-hydroxylase was tested by measuring the effect on the key enzymes in the biosynthesis of estradiol and dehydroepiandrosterone, CYP19 (aromatase) and CYP17 (17-lyase), respectively. Four compounds, VN/14-1, VN/50A-1, VN/65-4 and VN/66-1, were tested and all barely inhibited these CYP enzymes, even at concentration as high as 5 μM.

Enzyme Inactivation Activity of Acetylinic ATRA, Cyclopropyl-amine ATRA, and Cyclopropyl-ether-ATRA Acetylinic ATRA, 30, cyclopropyl-amine ATRA, 32, and cyclopropyl-ether-ATRA, 35, cause enzyme inactivation as a mechanism of their action. These three novel compounds are quite specific, because of the interaction with the enzyme's active site and their conversion to a form that binds to the enzyme either irreversibly or very tightly. These three novel compounds provide sustained enzymatic inhibition until new enzyme is synthesized. Thus, these three novel compounds have longer lasting effects and less side effects. To determine enzyme inactivation, hamster liver microsomes are preincubated with acetylinic ATRA, 30, cyclopropyl-amine ATRA, 32, or cyclopropyl-ether-ATRA, 35, as described above for 5, 10, 15, 20, or 60 minutes. The unbound acetylinic ATRA, 30, cyclopropyl-amine ATRA, 32, or cyclopropyl-ether-ATRA, 35, is then removed by charcoal treatment. The enzyme activity is then measured as described above, and the $K_i$ value of the inactivation reaction is calculated. The irreversible nature of the inhibition is demonstrated by incubating the pretreated enzyme preparation with a high concentration of substrate because if acetylinic ATRA, 30, cyclopropyl-amine ATRA, 32, or cyclopropyl-ether-ATRA, 35, is not tightly bound to the enzyme and is reversible, it would be possible to displace the inhibitor with excess amount of substrate. In addition, to demonstrate the irreversible nature of the inhibition, one dialyzes the pretreated enzyme preparation for various lengths of time to remove acetylinic ATRA, 30, cyclopropyl-amine ATRA, 32, or cyclopropyl-ether-ATRA, 35, which may dissociate slowly from the enzyme and then performs standard enzyme activity evaluation.

High Specificity for ATRA 4-hydroxylase (CYP26A1)

The high specificity of the novel C-4 substituted ATRA analogs for ATRA 4-hydroxylase is demonstrated by testing for inhibition of aromatase, CYP17, and other cytochrome P450s found in hamster liver microsome preparations. To demonstrate the lack of inhibition of cytochrome P450s enzymes (other than ATRA 4-hydroxylase), one measures the conversion of antipyrine (a well-known probe substrate for cytochrome P450s) to norantipyrine, and 4-hydroxy- and 3-hydroxymethyl-antipyrine using well-known techniques (Engle G, Hofmann U, Heidemann H, Cosme J, Eichelbaum M, *Antipyrine as a probe for human oxidative drug metabolism: identification of the cytochrome P450 enzymes catalyzing 4-hydroxyantipyrine, 3-hydroxymethylantipyrine, and norantipyrine formation*, Clin Pharm Thera 59: 613-623, 1996). To demonstrate the lack of inhibition of aromatase, one measures the conversion of [1β-$^3$H]androstenedione to estrone and estradiol using well-known techniques (Brodie et al, *The effect of an aromatase inhibitor, 4-hydroxy-4-androstene-3,17-dione, on estrogen-dependent processes in reproduction and breast cancer*, Endocrinology, June; 100 (6):1684-95, 1977). To demonstrate the lack of inhibition of CYP17, one measures the conversion of [21-$^3$H]17α-hydroxypregnenolone to dehydroepiandrosterone and androst-5-ene-3β, 17β-diol using well-known techniques (Njar V C O, Kato K, Nnane I P, Grigoryev D N, Long B J and Brodie A M H, *Novel 17-Azolyl Steroids; Potent Inhibitors of Human Cytochrome 17-Hydroxylase-C-17,20-Lyase (P45017): Potential Agents for the Treatment of Prostate Cancer*, J Med Chem 41: 902-912, 1998).

Inhibition of in vivo Catabolism of ATRA

In order to demonstrate that the novel compounds increase the biological half-life of exogenously administered ATRA and enhance ATRA's endogenous plasma levels, one determines the effects of the novel compounds on the plasma elimination of exogenously administered ATRA and also on the endogenous levels of the retinoid, using a well-known procedure (Van Wauwe et al., 1990). Rats weighing 200-220 g are treated p.o. with the novel compounds [e.g., 5, 10, 20, or 40 mg/kg prepared in polyethylene glycol 200 (PEG 200)] or vehicle (PEG 200) in a volume of 0.5 ml per 100 g body weight. One hour later, the animals are anesthetized with diethyl ether and injected i.v. with ATRA (0.1 mg/kg). At designated times (e.g., 10, 20, 30, 60, 90, 180, or 210 minutes) after injection, rats are sacrificed by decapitation and trunk blood collected on heparin (500 U/ml). After centrifugation (1000× g, 15 min), plasma fraction is recovered and processed immediately. The extracts are subjected to HPLC using conditions described above, eluent monitored by UV absorbance detection at 350 nm and ATRA is quantified by peak-area integration.

For experiments designed to assess the effects on endogenous plasma levels of ATRA, rats are treated p.o. with the novel compounds [e.g., 5, 10, 20, or 40 mg/kg prepared in polyethylene glycol 200 (PEG 200)] or vehicle (PEG 200) in a volume of 0.5 ml per 100 g body weight. The animals are sacrificed at various times (e.g., 1 hour intervals, up to 6 hours). Plasma is collected, processed and the levels of ATRA is determined by HPLC.

Retinoid Receptor Binding

Because the novel compounds are retinoid-related analogs, they bind to the retinoid receptors in vivo and thus have increased therapeutic potentials. Similar to ATRA, these novel compounds act as a ligand for the retinoic acid receptors (RARs, α, β, and γ) but not the retinoid X receptors (RXRs, α, β, and γ). To demonstrate that these novel C-4 substituted ATRA analogs are ligands for RAR but not RXRs, one uses a well-known assay system involving recombinant RAR and RXR protein expressed in *E. coli*. (Nervi C, Grippo J F, Sherman M I, George M D, Jetten A M, *Identification and characterization of nuclear retinoic acid-binding activity in human myeloblastic leukemia HL-60 cells*, Proc Natl Acad Sci USA 86: 5854-5858, 1989) The dissociation constants for the inhibitors is determined by the well described charcoal absorption method (Yang N, Schule R, Mangelsdorf D J, Evans R M, *Characterization of DNA binding and retinoic acid binding properties of retinoic acid receptor*, Proc Natl Acad Sci USA 88: 3559-3663, 1991). Briefly, serial dilutions of the novel compounds ($10^{-11}$ to $10^{-5}$ M) in dimethyl sulfoxide, 100 μL each is used. 12 mg of crude cytosolic extracts is prepared from pET15b (Novagen, Madison, Wis.)/hRAR-α, -β, and -γ prepared protein is used for each data point. All reactions are conducted in binding buffer (60 mM Na imidazole, 500 mM NaCl, 20 mM Tris, pH 7.9) for 14-16 hours at 4° C. in a final volume of 1 mL. Unbound [$^3$H]ATRA is removed by addition of 0.5 mL of equivalent-sized dextran-treated charcoal (final concentration 3% [wt/vol]) for 15 minutes at 4° C. Following centrifugation, 0.5 mL of supernatant is subjected to liquid scintillation counting. Binding in the presence of 100-fold excess of unlabeled ligand is defined as unspecific binding, while the total binding minus the nonspecific binding defines specific binding. The $IC_{50}$ values are obtained from logarithmic plots.

Retinoid Binding

Since the RAMBAs are retinoic acid analogs, it is possible that some of the compounds may bind to retinoid receptors and function as either transcriptional agonists/antagonists or may display anti AP-1 activity (Chambon P, *A decade of molecular biology of retinoic acid*, FASEB J 10: 5899-5904, 1996). The ability of three RAMBAs, VN/14-1, VN/50A-1 and VN/66-1 to bind to the individual RAR receptors was thus evaluated in vitro. Recombinant full-length RAR proteins were expressed as S-Tag fusion proteins in BL21 *E. coli* cells used for competitive binding assays. Each competition-binding assay contained 1 nM [³H] ATRA and various concentrations of the RAMBAs ranging from 1 nM to 500 nM. The specific binding of all-trans-RA in the absence of RAMBAs was set at 100%. $IC_{50}$ values for RARα and RARγ were approximately 16 nM for VN/14-1 while the $IC_{50}$ value for RARβ was approximately 200 nM. On the other hand, VN/50A-1 and VN/66-1 that do not possess the terminal free carboxylic acid moiety did not bind to any of the three RARs in vitro at concentrations up to 500 nM. Although Applicants do not wish to be bound by any particular mechanism of action, from these results it is believed that some of the compounds of the present invention possess RAR receptor mechanism of action as well as inhibition of ATRA 4-hydroxylase activity.

Inhibition of Prostate Cancer Proliferation In-vitro

The novel C-4 substituted ATRA analogs inhibit proliferation of prostate cancer in-vitro. Experiments are conducted on two prostate cancer cell lines, LNCaP cells and PC-3 cells. LNCaP cells are androgen-dependent cell cultures. PC-3 cells are androgen independent cell culture. LNCaP cells harbor both wild-type p53 and RB tumor-suppressor genes while PC-3 cells only express the wild-type RB gene and are null of p53 protein as a result of mutation. Thus, these two cell lines are used as representatives of hormone-dependent and independent human prostate cancer.

Methods

LNCaP cells are transferred into ATRA-free medium 3 days prior to start of experiments. Medium consist of phenol red-free IMEM supplemented with 5% FBS and 1% P/S. Cell are then plated into 24-well culture plates (15000 cells per well) in 1 mL of same medium. After a 24-hour attachment period, the vehicle (ethanol) or ATRA ($10^{-5}$ M) alone or ATRA in combination with a novel compound at a range of concentrations are added to triplicate wells. Medium/treatments are changed every 3 days. After 9 days of treatment, cells are removed from the wells with typsin/EDTA and counted in a Coulter counter. Using well-known methods (Wouters W, Van Dun J, Dillen A, Coene M.-C, Cools W and De Coster R, *Effects of liarozole, a new antitumoral compound an retinoic acid-induced inhibition of cell growth and on retinoic acid metabolism in MCF-7 breast cancer cells, Cancer Res* 52: 2841-2846, 1992), one determines the inhibitory effect of the novel compounds on LNCaP cells grown with ATRA.

This method also is repeated using PC-3 cells.

VN/14-1RA, VN/16-1RA, VN/17-1RA

Figure 8:
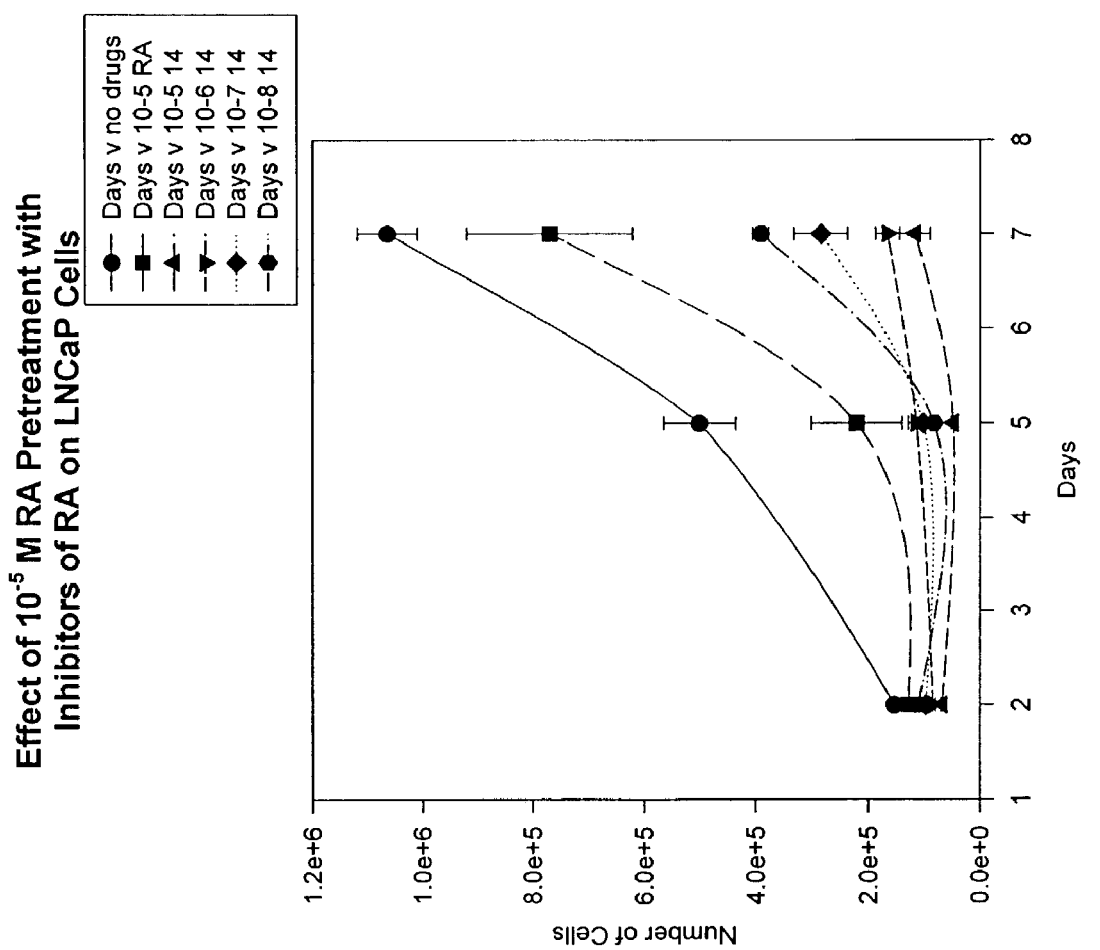
FIG. 8. VN/14-1RA and ATRA inhibition of growth of LNCaP cells.

FIG. 8 shows the inhibitory effects of VN/14-1RA in combination with ATRA on LNCaP cells. LNCaP cells growth curves in the presence of vehicle (no drug, ●), $10^{-5}$ M ATRA (■), $10^{-5}$ M ATRA combined with $10^{-8}$ M VN/14-1RA (✻), $10^{-5}$ M ATRA combined with $10^{-7}$ M VN/14-1RA (♦), $10^{-5}$ M ATRA combined with $10^{-6}$ M VN/14-1RA (▼), or $10^{-5}$ M ATRA combined with $10^{-5}$ M VN/14-1RA (▲). All dosages of VN/14-1RA in combination with ATRA inhibit the proliferation of LNCaP cells better than no drug or ATRA only. The two higher concentrations of VN/14-1RA ($10^{-5}$ M and $10^{-6}$ M) prevent the cells from increasing in number.

Figure 9:
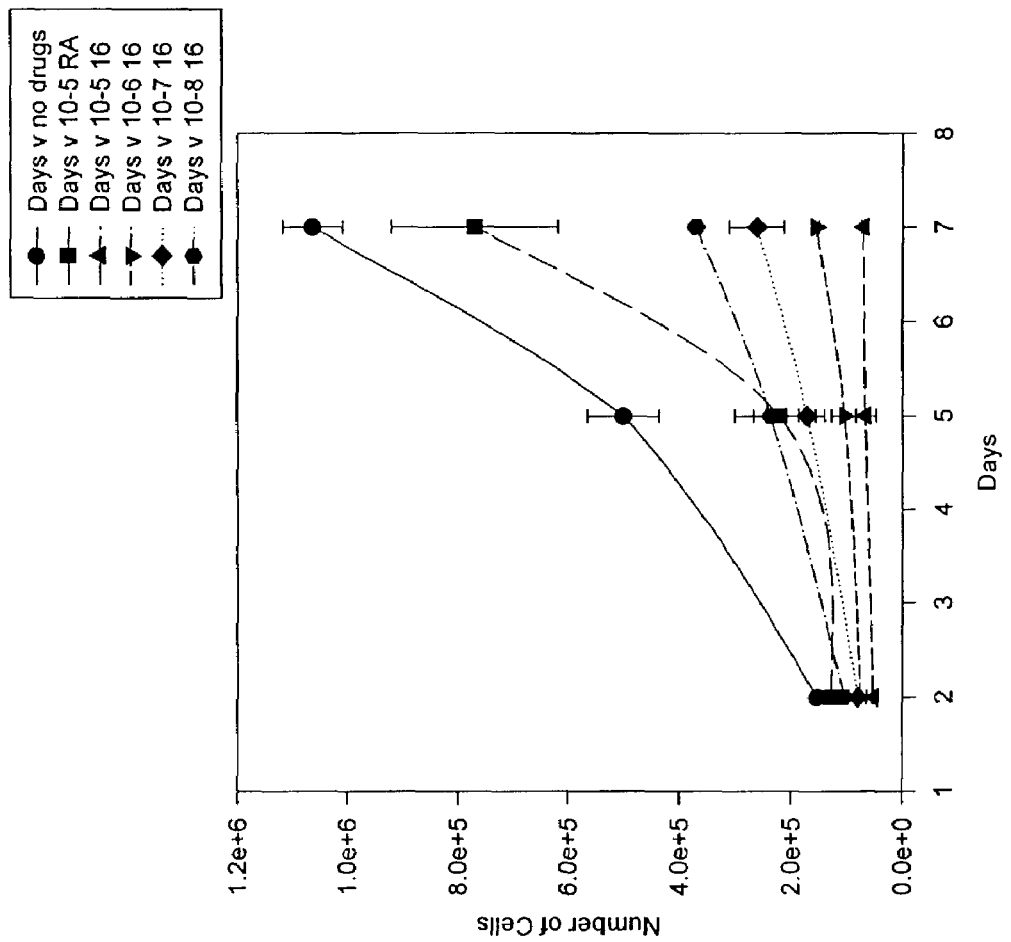
FIG. 9. VN/16-1RA and ATRA inhibition of growth of LNCaP cells.

FIG. 9 shows the inhibitory effects of VN/16-1RA in combination with ATRA on LNCaP cells. LNCaP cells growth curves in the presence of vehicle (no drug, ●), $10^{-5}$ M ATRA (■), $10^{-5}$ M ATRA combined with $10^{-8}$ M VN/16-1RA (✻), $10^{-5}$ M ATRA combined with $10^{-7}$ M VN/16-1RA (♦), $10^{-5}$ M ATRA combined with $10^{-6}$ M VN/16-1RA (▼), or $10^{-5}$ M ATRA combined with $10^{-5}$ M VN/16-1RA (▲). All dosages of VN/16-1RA in combination with ATRA inhibit the proliferation of LNCaP cells better than no drug or ATRA only. The highest concentration of VN/16-1RA ($10^{-5}$ M) stop the cells from increasing in number.

Figure 10:
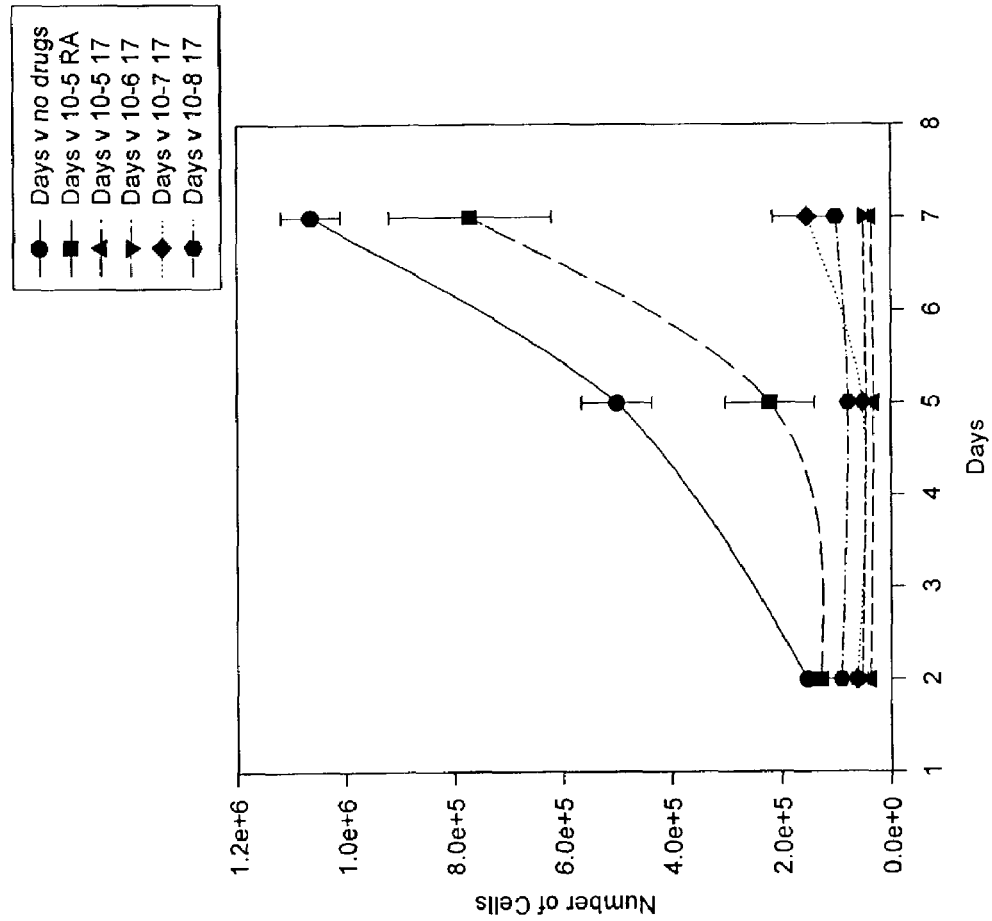
FIG. 10. VN/17-1RA and ATRA inhibition of growth of LNCaP cells.

FIG. 10 shows the inhibitory effects of VN/17-1RA in combination with ATRA on LNCaP cells. LNCaP cells growth curves in the presence of vehicle (no drug, ●), $10^{-5}$ M ATRA (■), $10^{-5}$ M ATRA combined with $10^{-8}$ M VN/17-1RA (✻), $10^{-5}$ M ATRA combined with $10^{-7}$ M VN/17-1RA (♦), $10^{-5}$ M ATRA combined with $10^{-6}$ M VN/17-1RA (▼), or $10^{-5}$ M ATRA combined with $10^{-5}$ M VN/17-1RA (▲). All dosages of VN/17-1RA in combination with ATRA inhibit the proliferation of LNCaP cells better than no drug or ATRA only. All concentrations of VN/17-1RA are effective in preventing the cells from increasing in number.

Figure 11:
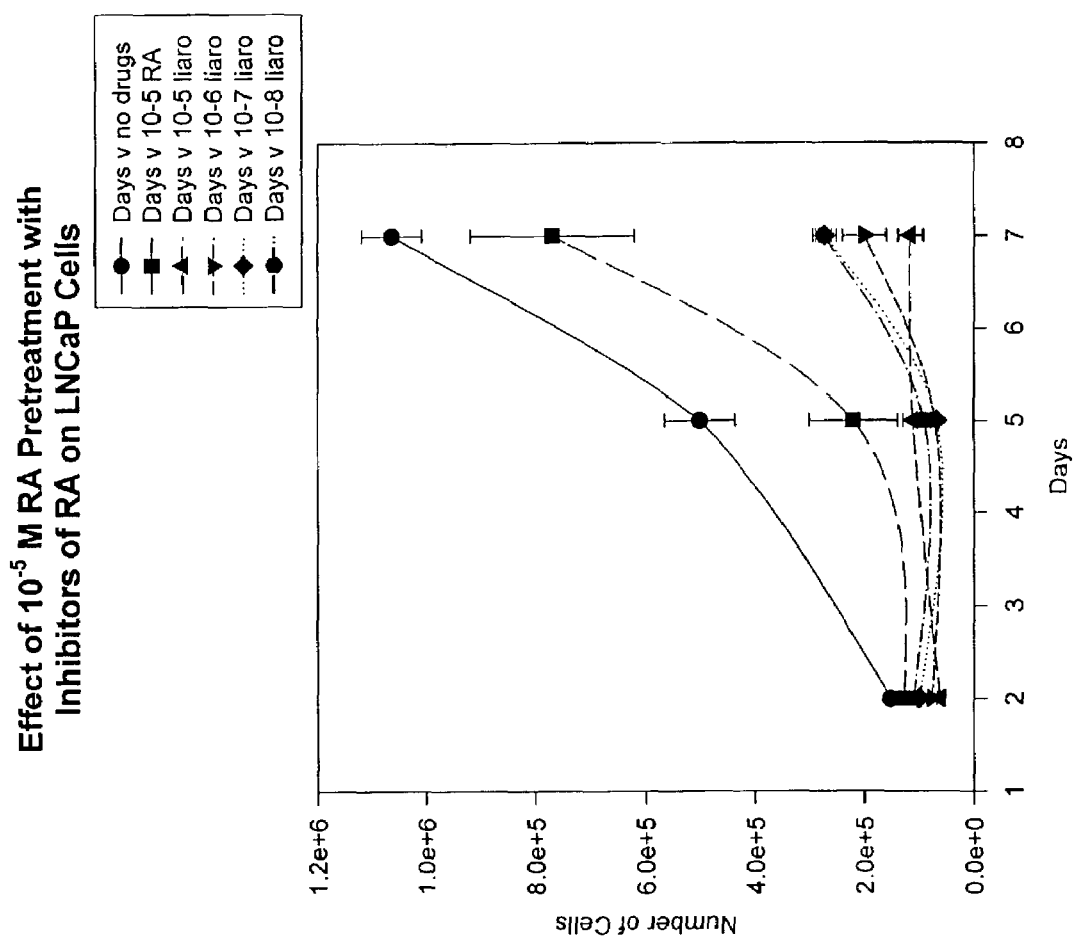
FIG. 11. Liarozole and ATRA inhibition of growth of LNCaP cells.

As a comparison, FIG. 11 shows the inhibitory effects of liarozole in combination with ATRA on LNCaP cells. LNCaP cells growth curves in the presence of vehicle (no drug, ●), $10^{-5}$ M ATRA (■), $10^{-5}$ M ATRA combined with $10^{-8}$ M liarozole (✻), $10^{-5}$ M ATRA combined with $10^{-7}$ M liarozole (♦), $10^{-5}$ M ATRA combined with $10^{-6}$ M liarozole (▼), or $10^{-5}$ M ATRA combined with $10^{-5}$ M liarozole (▲). Liarozole when combined with ATRA also inhibit the proliferation of LNCaP cells better than no drug or ATRA only. Only the highest concentration of liarozole ($10^{-5}$ M) prevents the cells from increasing in number.

Figure 16:
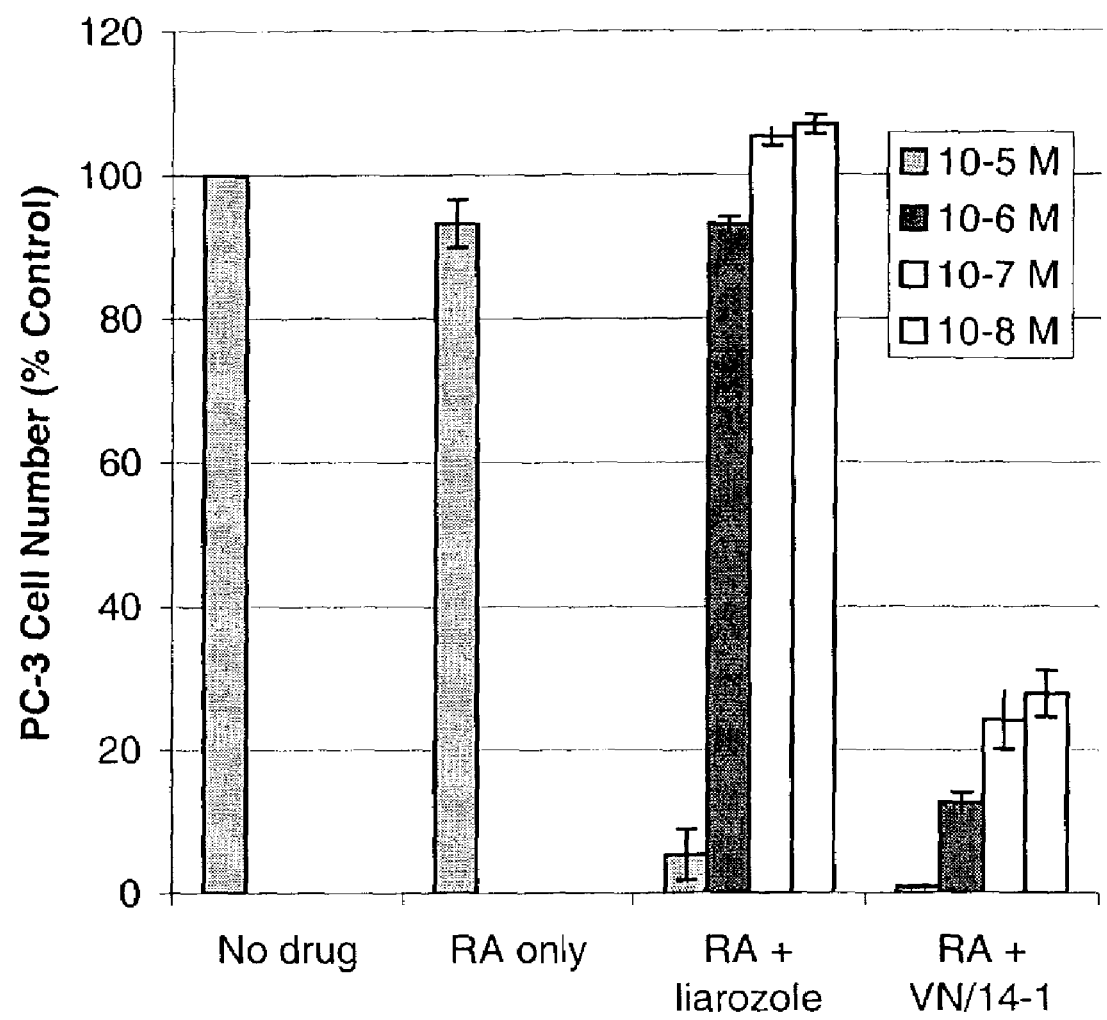
FIG. 16: Effect of ATRA (1 nM) Alone or in Combination with Liarozole or VN/14-1 on PC-3 Cell Growth

FIG. 16 shows the results of a representative experiment comparing the antiproliferative effects of VN/14-1 and liarozole. PC-3 cells were incubated with test compounds for 9 days with medium changes on days 2, 5, and 7 and proliferation assessed as described above. The results show that VN/14-1 is clearly more effective than liarozole.

Inhibition of Prostate Cancer and Breast Cancer in-vivo

The anti-proliferative effects of the novel compounds on prostate cancer is demonstrated by administering the novel compounds to SCID mice which have been implanted with LNCaP cells or PC-3 cells. These LNCaP cells and PC-3 cells develop into tumors in SCID mice. Because the mechanism of growth simulations are different, but together display many of the properties of clinical prostate cancer, the models provide an indication of efficacy in humans. In addition, one can demonstrate the anti-proliferative effects of the novel compounds on breast cancer by administering the novel compounds to SCID mice which have been implanted with MCF-7Ca cells which develop into tumors in SCID mice.

Methods

LNCaP cells are cultured as described above. Subconfluent cell are scraped into DPBS, counted and suspended in Matrigel ($3 \times 10^7$ cells/mL). Male SCID mice 4-6 weeks old are obtained from NCI, Frederick, Md. Each mouse is inoculated s.c. with 0.1 mL of the cell suspension at two sites. Growth rate are determined from tumor volumes using calipers using well-known techniques (Yue W, Wang J, Savinov A, Brodie A, *Effect of aromatase inhibitors on growth of mammary tumors in a nude mouse model, Cancer Res*, July 15;55(14):3073-7 (1995). Tumor volumes are calculated according to the equation: $V = 4/3 \times \pi \times r_1^2 \times r_2$ ($r_1 < r_2$). Tumors are allowed to grow for 4-5 weeks following cell inoculation. Mice are then grouped (6 mice per group) for castration or treatment with vehicle, liarozole (as a comparison), or one of the C-4 substituted ATRA analogs (at various concentration based on $IC_{50}$ and/or $K_i$ values for each novel compound, mg/kg/day). The route of administration of C-4 substituted ATRA analogs include s.c., i.m., i.p., and oral. Tumors are measured weekly for 4-5 weeks of treatment and tumor volumes calculated. Blood is collected from the euthanized animals that are autopsied 1 hour after the last injection. Tumors are excised, weighed and stored at −80° C. until required. This standard well-known test for evaluating compounds for antitumor efficacy in LNCaP tumors in SCID mice is described in Grigoryev D N, Kato K, Njar V C O, Long B J, Ling Y, Wang X, Mohler J and Brodie A M H, *Cytochrome P450c17 expressing E. coli as a first-step Screening System for 17-hydroxylase-C17,20-Lyase Inhibitors*, Anal Biochem 267: 319-330, 1999a, and in Grigoryev D N, Long B J, Njar V C O, Liu Y, Nnane I P and Brodie A M H, *Effects of New 17-Hydroxylase/C17,20-Lyase Inhibitors on LNCaP Prostate Cancer Cell Growth, In Vitro and In Vivo*. Brj Cancer Cancer 81: 622-630, 1999b.

For PC-3 tumors, one utilizes the same methods.

For MCF-7Ca tumors, one utilizes the same methods, except the SCID mice are female, receive ovariectomies, and receive androstenedione (0.1 mg/day).

VN/14-1RA

Figure 12:
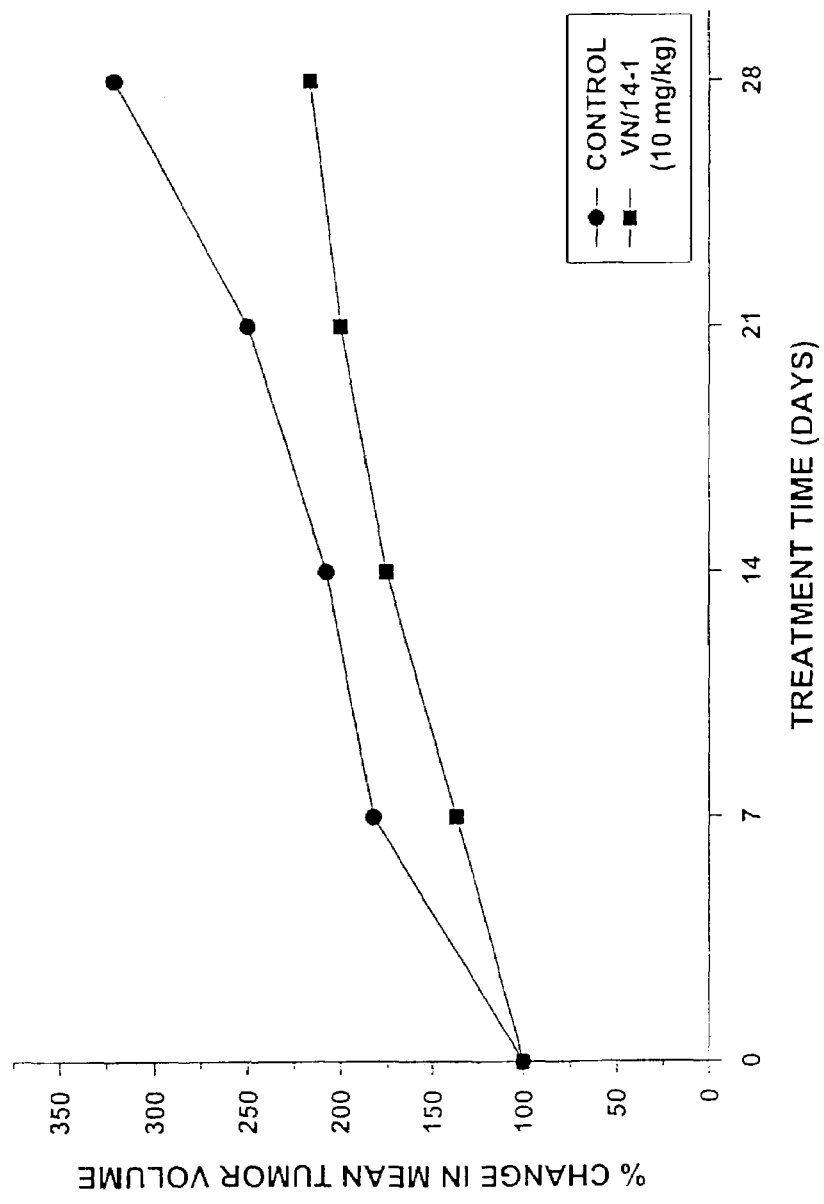
FIG. 12. VN/14-1RA inhibition of growth of MCF-7Ca tumors in nude mice.

As shown in FIG. 12, when 10 mg/kg of VN/14-1RA is administered to mice with MCF-7Ca tumors, the tumors do not increase in size as fast as tumors in the control group. After twenty-eight days, VN/14-1RA given at 10 mg/kg slows the proliferation of the tumors to one-half the size of the tumors in the control group. VN/14-1RA is shown as ■; control is shown as ●.

Induction of ATRA Metabolism

Figure 17:
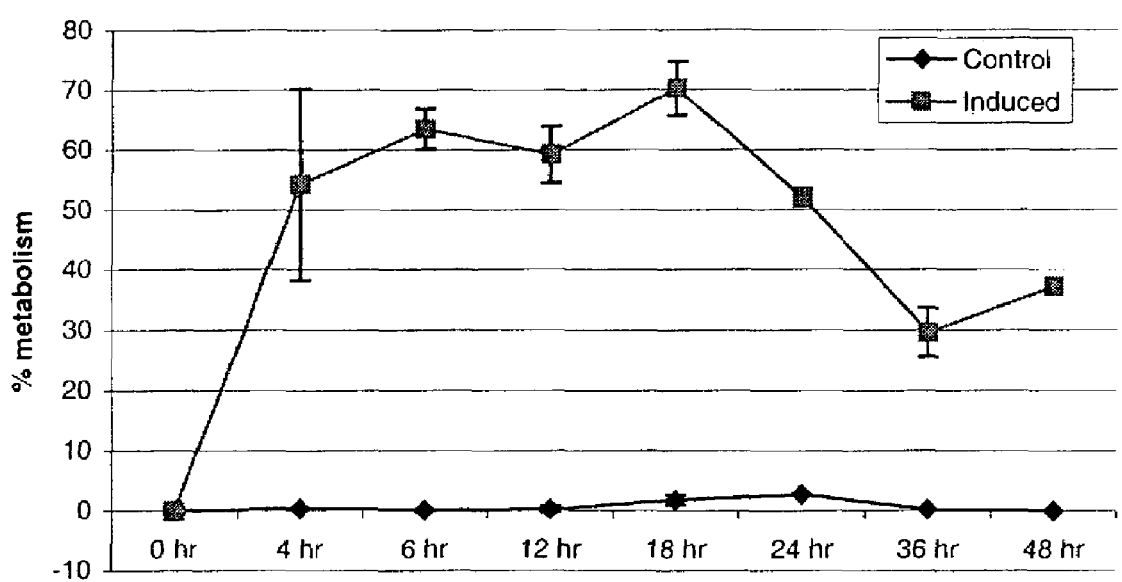
FIG. 17: Metabolism of 0.8 µM 3H-ATRA Following Induction with 1 µM ATRA in LNCaP Cells.

The potential of these cell lines to metabolize ATRA was investigated. Both LNCaP and PC-3 cell lines did not show constitutive ATRA catabolism. However, induction of ATRA 4-hydroxylase activity was observed in LNCaP cells, but not in PC-3 cells. LNCAP cells were preincubated with 1.0 μM ATRA for different time periods up to 48 hour. Following preincubation, ATRA metabolism was determined using 0.8 μM [11,12-$^3$H]ATRA. Induction of 4-hydroxylase activity ([$^3$H]ATRA metabolism was time-dependent with a fast onset and maximal induction achieved after a preincubation period of 18 hour (FIG. 17).

From these data the mechanism by which VN/14-1 enhanced the ability of ATRA to inhibit LNCaP cell proliferation (FIG. 8) is believed to be due to inhibition of ATRA 4-hydroxylase activity. On the other hand, since ATRA 4-hydroxylase is not present in PC-3 cells, it is believed that the growth-inhibiting property of VN/14-1 is due to binding to retinoid receptor(s). It is believed that VN/14-1 can bind to retinoid receptor and function as either transcriptional agonist/antagonist or it displays anti AP-1 activity. VN/14-1 binds with high affinity to RARα and RARγ receptors. Thus, the compounds of the present invention are believed to have effects not only on ATRA 4-hydroxylase, but also bind to the RAR receptors.

Pharmacokinetic (PK) Studies

Figure 18:
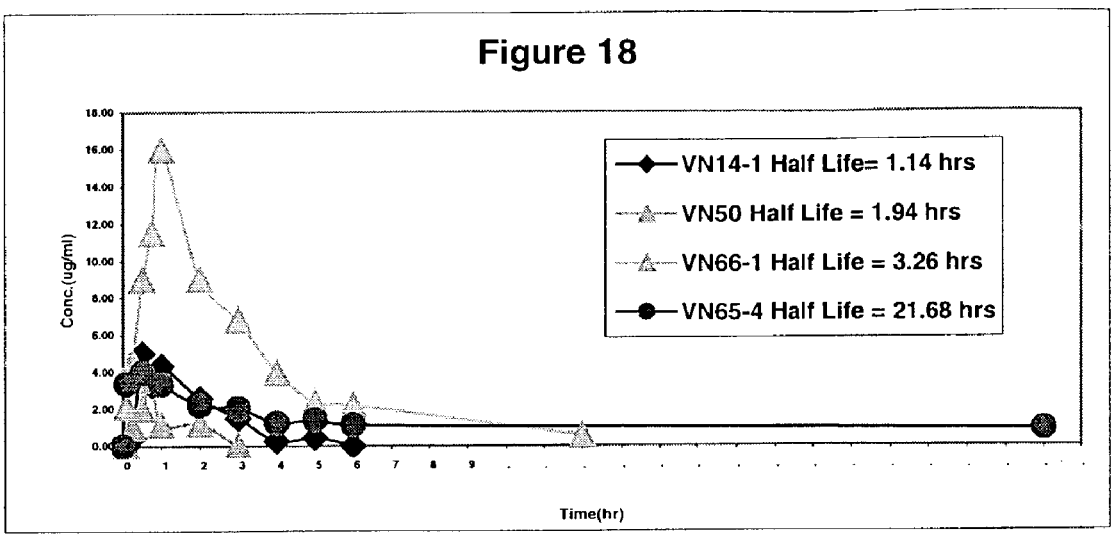
FIG. 18: Plasma Levels in Balb/c Mice Following Dose of 10 mg/kg body weight Given s/c.

Pharmacokinetic studies of VN/65-4 and VN/66-1 were measured in mice and were compared to VN/14-1 and VN/50A-1. Mice were dosed s.c. at 10 mg/kg using a vehicle, 45% β-cyclodextrin in water, and plasma levels were measured by HPLC. In vivo, VN/65-4 was rapidly and completely converted to corresponding acid. The results are summarized in Table 3 below and the profiles in FIG. 18.

TABLE 3

Pharmacokinetic Parameters in Mice[a]

| Compound | $C_{max}$ (μg/ml) | $T_{max}$ (hr) | $t_{1/2}$ (hr) | AUC (μ/ml min) |
|---|---|---|---|---|
| VN/14-1 | 5.02 | 0.50 | 1.14 | 567.80 |
| VN50A-1 | 3.58 | 0.75 | 1.94 | 176.60 |
| VN/65-4 | 4.00 | 0.50 | 21.68 | 1758.90 |
| VN/66-1 | 16.00 | 1.0 | 3.36 | 2872.50 |

[a]All compounds were dosed at 10 mg/kg s.c. Values are average of two animals.

VN/65-4 and VN/66-1 appear substantially better than either VN/14-1 or VN/50A-1, with an especially dramatic improvement in $t_{1/2}$ (1.14 hour for VN/14-1 versus 21.68 hour for VN/65-4) and AUC. For VN/66-1, there was a dramatic improvement in $C_{max}$ (5.02 μg/ml for VN/14-1 versus 16.0 μg/ml for VN/66-1) and a significant change in AUC and $t_{1/2}$. From these favorable PK parameters of VN/65-4 and VN/66-1it is believed that the compounds can effectively enhance endogenous ATRA levels that results in increased antitumor activity of ATRA.

Effects of VN/65-4 on Plasma Elimination of ATRA

Figure 19:
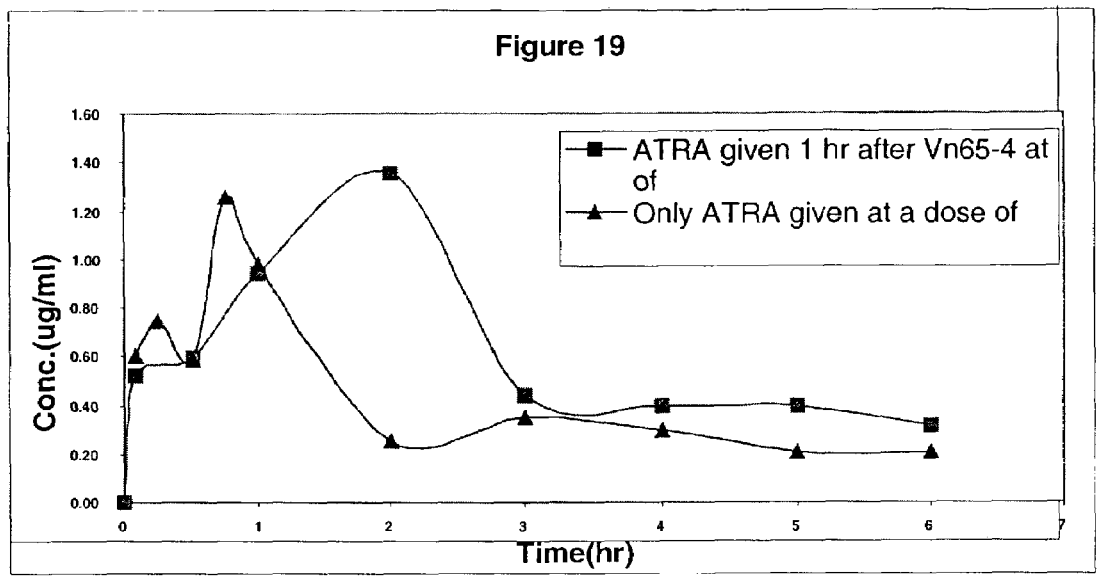
FIG. 19: Plasma Concentration of ATRA (1 mg/kg) After a Dose of 10 mg/kg body weight of VN/65-4.

To determine the ability of VN/65-4 to delay the velocity of plasma elimination of ATRA, mice were treated s.c. with VN/65-4 (10 mg/kg). One hour later, the mice were administered s.c. ATRA (1.0 mg/kg) and sacrificed at various time points. As shown in FIG. 19, VN/65-4 delayed the rate of ATRA elimination significantly, altering AUC, $T_{max}$, $t_{1/2}$ and $C_{max}$. From these experiments it is believed that it is possible to improve ATRA efficacy by reducing its enhanced metabolism to increase endogenous levels.

Growth Effects on PC-3 Tumors Grown in Male Nude Mice

Figure 20:
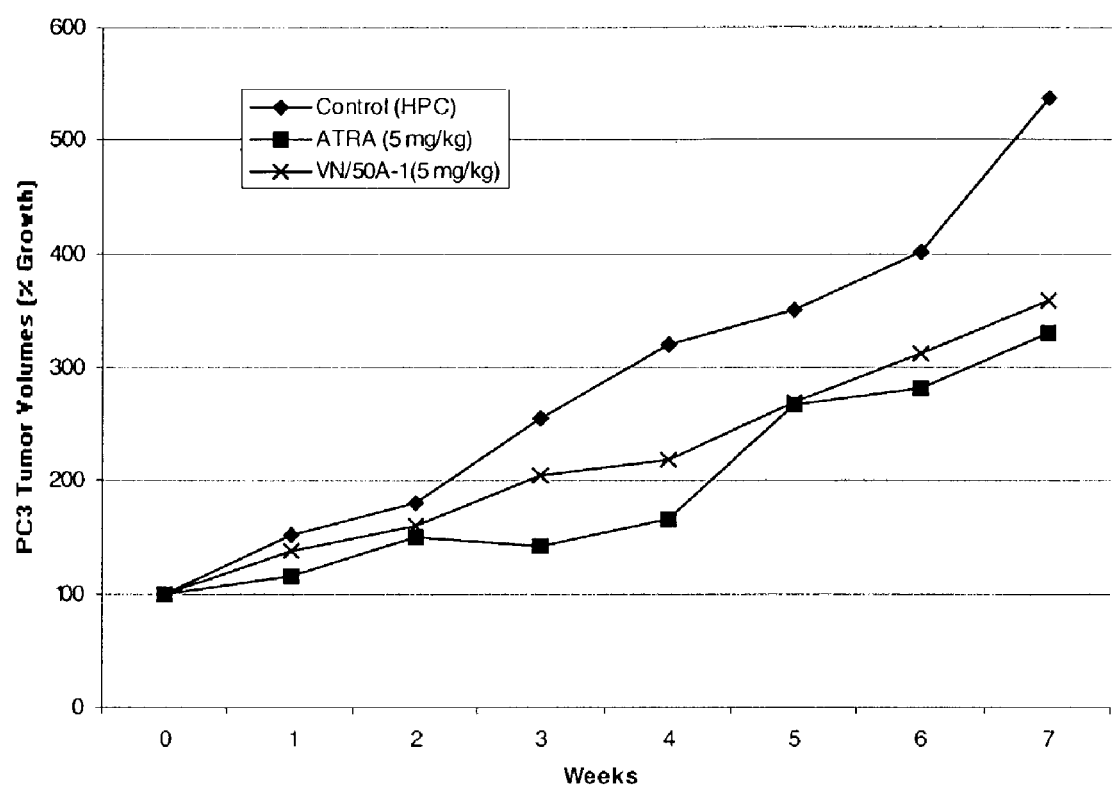
FIG. 20: Effect of ATRA and VN/50A-1 on PC 3 Tumor Volumes in Male Nude Mice

The effects of VN/50A-1 on tumor growth was determined in mouse xenografts and compared to ATRA as the reference treatment (FIG. 20). Mice were grouped 35 days after cell inoculation when measurable tumor volume was approximately 500 mm$^3$. Total tumor volume in the control mice increased 5.4-fold over 7 weeks and tumor volume in the mice treated with ATRA increased by 3.2-fold (41% reduction compared with control). In the mice treated with VN/50A-1, tumor volume increased by 3.5-fold, which was 38% reduction versus control mice, which correlated well with accumulation of ATRA in plasma and in tumors. Tumor weights in the ATRA and VN/50A-1 were significantly (P<0.05) lower than those in the control mice. VN/50A-1 is completely eliminated from plasma within 3 hour of administration to mice (see FIG. 18). The inventive compounds with longer half-lives will have favorable bioavilability and are expected to be more efficacious.

From the potent antiproliferative effects of the compounds of the present invention against LNCaP and PC-3 cells it is believed that the compounds of the present invention (with additional mechanism of action, via retinoid receptor interaction) are efficacious in biologically diverse prostate cancers.

International Application Number PCT/US01/16524 and U.S. Provisional Patent Application 60/217,465 are herein incorporated by reference.

While the invention has been described in detail and with reference to specific embodiments thereof, it will be apparent to one of ordinary skill in the art that various changes and modifications can be made therein without departing from the spirit and scope thereof. The artisan will further acknowledge that the Examples recited herein are demonstrative only and are not meant to be limiting.

The invention claimed is:
1. A chemical compound, or pharmaceutically acceptable salt thereof, having the formula (I)

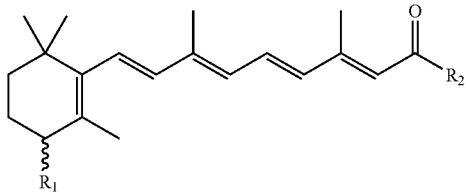

wherein $R_1$ and $R_2$ are selected from one of the following Substituent Set 1 or Substituent Set 2:

Substituent Set 1:
$R_1$ is selected from the group consisting of a thiol, cyano, amino, azido, cyclopropylamino, a pyridyl group, an allylic azole group, and $C_1$ to $C_{10}$ alkyl thiol;
or $R_1$ is —$OR_4$, where $R_4$ is hydrogen, methyl, ethyl or cyclopropylether or forms, together with the 4-position carbon, an oxirane;
or $R_1$ is —$NR_5R_6$, where $R_5$ and $R_6$ are independently selected from the group consisting of hydrogen and C1 to C10 alkyl; or $R_5$ and $R_6$ together form an imidazolyl ring or a triazole ring;
or $R_1$ forms, together with the 4-position carbon, a thiirane;
or $R_1$ forms, together with the 4-position carbon, an aziridine or an oxime and
$R_2$ is selected from the group consisting of aminophenol and —$OR_3$, wherein $R_3$ is selected from the group consisting of a phenyl, naphthyl, azole, and a heterocyclic group; wherein said heterocyclic group is selected from the group consisting of piperidinyl, piperazinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoazolyl, furyl, tetrahydrofuryl, tetrahydropyranyl, thienyl, benzothienyl, thiamorpholinyl, thiamorpholinylsulfoxide, thiamorpholinylsulfone, oxadiazolyl, triazolyl, tetrahydroquinolinyl, and tetrahydroisoquinolinyl;

Substituent Set 2:
$R_1$ is selected from the group consisting of a thiol, cyano, amino, azido, cyclopropylamino, a pyridyl group, an allylic azole group, methyleneazolyl, and $C_1$ to $C_{10}$ alkyl thiol;
or $R_1$ is —$OR_4$, where $R_4$ is methyl, ethyl, cyclopropylether, or forms, together with the 4-position carbon, an oxirane;
or $R_1$ is —$NR_5R_6$, where $R_5$ and $R_6$ are independently selected from the group consisting of hydrogen and C1 to C10 alkyl; or $R_5$ and $R_6$ together form an imidazolyl ring or a triazole ring;
or $R_1$ forms, together with the 4-position carbon, a thiirane;
or $R_1$ forms, together with the 4-position carbon, an aziridine or an oxime; and
$R_2$ is selected from the group consisting of hydroxyl, methoxy, aminophenol, and —$OR_3$, wherein $R_3$ is selected from the group consisting of a phenyl, naphthyl, azole, and a heterocyclic group; wherein said heterocyclic group is selected from the group consisting of piperidinyl, piperazinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoazolyl, furyl, tetrahydrofuryl, tetrahydropyranyl, thienyl, benzothienyl, thiamorpholinyl, thiamorpholinylsulfoxide, thiamorpholinylsulfone, oxadiazolyl, triazolyl, tetrahydroquinolinyl, and tetrahydroisoquinolinyl.

2. The chemical compound as in claim 1, wherein $R_1$ and $R_2$ are selected from said Substituent Set 2, and $R_2$ is hydroxyl.

3. The chemical compound as in claim 1, wherein $R_1$ and $R_2$ are selected from said Substituent Set 2, and $R_2$ is —$OCH_3$.

4. The chemical compound as in claim 1, wherein $R_1$ is a thiol or alkylthiol, or $R_1$ forms, together with the 4-position carbon, a thiirane.

5. The chemical compound as in claim 1, wherein $R_1$ is —$OR_4$, where $R_4$ is methyl or ethyl.

6. The chemical compound as in claim 1, wherein $R_1$ is cyclopropylether or forms, together with the 4-position carbon, an oxirane.

7. The chemical compound as in claim 1, wherein $R_1$ is —$NR_5R_6$, where $R_5$ and $R_6$ are independently selected from the group consisting of hydrogen and a C1 to C10 alkyl; or $R_5$ and $R_6$ together form an imidazolyl ring or a triazole ring.

8. The chemical compound as in claim 7, wherein $R_5$ and $R_6$ together form an imidazolyl ring or a triazole ring.

9. The chemical compound as in claim 8, wherein $R_5$ and $R_6$ together form an imidazolyl ring.

10. The chemical compound as in claim 9, wherein $R_2$ is an imidazolyl ring.

11. The chemical compound as in claim 9, wherein the compound is (±)-4-(1H-imidazol-1-yl)-13-cis-methylretinoate or a pharmaceutically acceptable salt thereof.

12. The chemical compound as in claim 9, wherein the compound is (±)-4-(1H-imidazol-1-yl)-N-(4'-hydroxyphenol)retinamide, or a pharmaceutically acceptable salt thereof.

13. The chemical compound as in claim 9, wherein the compound is (±)-4-(1H-imidazol-1-yl)-13-cis-retinoic acid or a pharmaceutically acceptable salt thereof.

14. The chemical compound as in claim 9, wherein the compound is (±)-4-(1H-imidazol-1-yl)-13-cis-retinoyl-imidazole or a pharmaceutically acceptable salt thereof.

15. The chemical compound as in claim 9, wherein the compound is (±)-4-(1H-imidazol-1-yl)-N-(4'-hydroxyphenol)13-cis-retinamide or a pharmaceutically acceptable salt thereof.

16. The chemical compound as in claim 1, wherein $R_1$ is selected from the group consisting of a cyano group, an amino group, an azido group, and a cyclopropylamino group; or $R_1$ forms, together with the 4-position carbon, an aziridine group or an oxime group.

17. The chemical compound as in claim 1, wherein $R_1$ is a pyridyl group.

18. The chemical compound as in claim 1, wherein $R_1$ is an allylic azole group.

19. The chemical compound as in claim 18, wherein $R_1$ is a methyleneazolyl group.

20. The chemical compound as in claim 1, wherein the compound is formula (II)

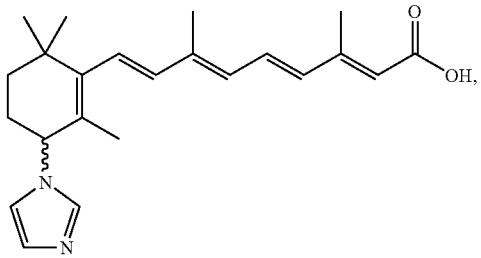

(II)

or a pharmaceutically acceptable salt thereof.

21. The method of synthesizing the chemical compound as in claim 20, comprising the steps of:
   contacting (±)-4-hydroxymethyl retinoate with carbonyldiimidazole in $CH_3CN$ at room temperature to obtain (±)-4-(1H-imidazol-1-yl)methyl retinoate; and
   hydrolysizing (±)-4-(1H-imidazol-1-yl)methyl retinoate in refluxing methanolic KOH to obtain (±)-4-(1H-imidazol-1-yl)retinoic acid.

22. The chemical compound as in claim 1, wherein the compound is formula (III)

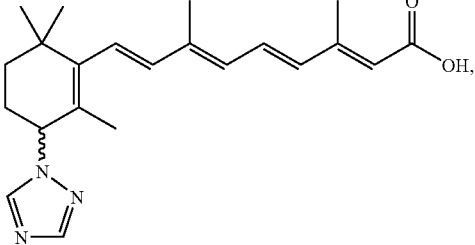

(III)

or a pharmaceutically acceptable salt thereof.

23. The method of synthesizing the chemical compound as in claim 22, comprising the steps of:
   contacting (±)-4-hydroxymethyl retinoate with carbonylditriazole in $CH_3CN$ at room temperature to obtain (±)-4-(1H-1,2,4-triazol-1-yl)methyl retinoate; and
   hydrolysizing of (±)-4-(1H-1,2,4-triazol-1-yl)methyl retinoate in refluxing methanolic KOH to obtain (±)-4-(1H-1,2,4-triazol-1-yl)retinoic acid.

24. The chemical compound as in claim 1, wherein the compound is formula (IV)

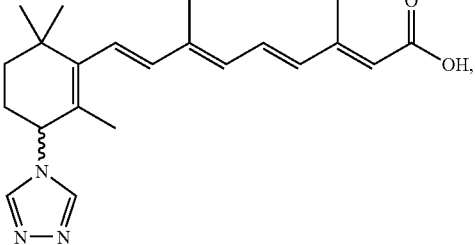

(IV)

or a pharmaceutically acceptable salt thereof.

25. The method of synthesizing the chemical compound as in claim 24, comprising the steps of:
   contacting (±)-4-hydroxymethyl retinoate with carbonylditriazole in $CH_3CN$ at room temperature to obtain (±)-4-(1H-1,2,4-triazol-1-yl)methyl retinoate; and
   hydrolysizing (±)-4-(1H-1,2,4-triazol-1-yl)methyl retinoate in refluxing methanolic KOH to obtain (±)-4-(1H-1,2,4-triazol-1-yl)retinoic acid.

26. A method of treating a mammal having a cancer comprising administering a therapeutically effective amount of at least one compound of claim 1 to the mammal having the cancer, wherein the cancer is selected from the group consisting of prostate and breast.

27. The method of claim 26, wherein said mammal has a prostate cancer.

28. The method of claim 26 wherein said mammal is a human.

29. A pharmaceutical composition comprising a compound selected from the group consisting of:
   (±)-4-(1H-imidazole-1-yl)retinoic acid or a pharmaceutically acceptable salt thereof,
   (±)-4-(1H-1,2,4-triazol-1-yl)retinoic acid or a pharmaceutically acceptable salt thereof,
   (±)-4-(1H-imidazol-1-yl)-13-cis-methylretinoate or a pharmaceutically acceptable salt thereof,
   (±)-4-(1H-imidazol-1-yl)-N-(4-hydroxyphenol)retinamide or a pharmaceutically acceptable salt thereof,
   (±)-4-(1H-imidazol-1-yl)-13-cis-retinoic acid or a pharmaceutically acceptable salt thereof,
   (±)-4-(1H-imidazol-1-yl)-13-cis-retinoyl-imidazole or a pharmaceutically acceptable salt thereof, and
   (±)-4-(1H-imidazol-1-yl)-N-(4'-hydroxyphenol) 13-cis-retinamide or a pharmaceutically acceptable salt thereof,
   and a pharmaceutically acceptable inactive ingredient.

30. The pharmaceutical composition of claim 29, wherein said pharmaceutically acceptable inactive ingredient is at least one member selected from the group consisting of a diluent, a carrier, a solvent, a disintegrating agent, a lubricant, a stabilizer, and a coating.

31. The pharmaceutical composition of claim 29, wherein the composition is formulated for oral administration.

32. The pharmaceutical composition of claim 29, wherein the composition is formulated for parenteral administration.

33. The pharmaceutical composition of claim 29, wherein the composition is formulated for administration by injection.

34. A pharmaceutical composition comprising the compound of claim 1 and a pharmaceutically acceptable inactive ingredient.

35. The pharmaceutical composition as claimed in claim 29 further comprising all-trans retinoic acid (ATRA).

36. The method of claim 26, wherein said cancer is breast cancer.

37. A pharmaceutical composition comprising at least one compound selected from the group consisting of:
   (±)-4-(1H-imidazol-1-yl)methylretinoate or a pharmaceutically acceptable salt thereof,
   (±)-4-(1H-1,2,4-triazol-1-yl)methylretinoate or a pharmaceutically acceptable salt thereof,
   (±)-4-(4H-1,2,4-triazol-4-yl)methylretinoate or a pharmaceutically acceptable salt thereof,
   (±)-4-(4H-1,2,4-triazol-4-yl)retinoic acid or a pharmaceutically acceptable salt thereof,
   (±)-4-(1H-imidazol-1-yl)-N-(imidazolyl)retinamide or a pharmaceutically acceptable salt thereof,
   (±)-4-(hydroxyimino)methylretinoate or a pharmaceutically acceptable salt thereof, and
   (±)-4-(1H-imidazol-1-yl)-N-(imidazolyl)-13-cis-retinamide or a pharmaceutically acceptable salt thereof;
   and a pharmaceutically acceptable inactive ingredient.

* * * * *